US010875860B2

(12) United States Patent
Cushman et al.

(10) Patent No.: US 10,875,860 B2
(45) Date of Patent: Dec. 29, 2020

(54) AZAINDENOISOQUINOLINE COMPOUNDS AND USES THEREOF

(71) Applicants: Purdue Research Foundation, West Lafayette, IN (US); THE UNITED STATES OF AMERICA, as represented by the Secretary, Department of Health and Human Services, Bethesda, MD (US)

(72) Inventors: Mark S. Cushman, West Lafayette, IN (US); Ping Wang, Vestavia Hills, AL (US); Yves George Pommier, Bethesda, MD (US); Mohamed S. A. Elsayed, Urbana, IL (US)

(73) Assignees: PURDUE RESEARCH FOUNDATION, West Lafayette, IN (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/471,945

(22) PCT Filed: Dec. 19, 2017

(86) PCT No.: PCT/US2017/067206
§ 371 (c)(1),
(2) Date: Jun. 20, 2019

(87) PCT Pub. No.: WO2018/118852
PCT Pub. Date: Jun. 28, 2018

(65) Prior Publication Data
US 2020/0095243 A1 Mar. 26, 2020

Related U.S. Application Data

(60) Provisional application No. 62/437,777, filed on Dec. 22, 2016.

(51) Int. Cl.
*C07D 471/04* (2006.01)
*A61K 45/06* (2006.01)
*A61P 35/04* (2006.01)

(52) U.S. Cl.
CPC ........... *C07D 471/04* (2013.01); *A61P 35/04* (2018.01); *A61K 45/06* (2013.01)

(58) Field of Classification Search
CPC ........ C07D 471/04; A61P 35/04; A61K 45/06
See application file for complete search history.

(56) References Cited

U.S. PATENT DOCUMENTS

| 5,023,261 | A | 6/1991 | Kamijo et al. |
| 6,509,344 | B1 | 1/2003 | Cushman et al. |
| 6,828,319 | B2 | 12/2004 | Jagtap et al. |
| 7,312,228 | B2 | 12/2007 | Cushman et al. |
| 7,495,100 | B2 | 2/2009 | Cushman et al. |
| 7,781,445 | B2 | 8/2010 | Cushman et al. |
| 8,053,443 | B2 | 11/2011 | Cushman et al. |
| 8,686,146 | B2 | 4/2014 | Cushman et al. |
| 8,829,022 | B2 | 9/2014 | Cushman et al. |
| 8,912,213 | B2 | 12/2014 | Cushman et al. |
| 9,034,870 | B2 | 5/2015 | Cushman et al. |
| 9,073,920 | B2 | 7/2015 | Cushman et al. |
| 9,175,002 | B2 | 11/2015 | Cushman et al. |
| 9,206,193 | B2 | 12/2015 | Cushman et al. |
| 9,217,010 | B2 | 12/2015 | Cushman et al. |
| 9,328,073 | B2 | 5/2016 | Cushman et al. |
| 9,388,211 | B2 | 7/2016 | Cushman et al. |
| 9,399,660 | B2 | 7/2016 | Cushman et al. |
| 9,402,842 | B2 | 8/2016 | Cushman et al. |
| 9,682,990 | B2 | 6/2017 | Cushman et al. |
| 9,796,753 | B2 | 10/2017 | Cushman et al. |
| 2005/0010046 | A1 | 1/2005 | LaVoie et al. |
| 2006/0025595 | A1 | 2/2006 | Cushman et al. |
| 2006/0247211 | A1 | 11/2006 | Cushman et al. |
| 2008/0090831 | A1 | 4/2008 | LaVoie et al. |
| 2008/0242692 | A1 | 10/2008 | Cushman et al. |
| 2008/0318995 | A1 | 12/2008 | Cushman et al. |
| 2012/0101119 | A1 | 4/2012 | Cushman et al. |
| 2012/0302563 | A1 | 11/2012 | Cushman et al. |
| 2013/0345252 | A1 | 12/2013 | Cushman et al. |

(Continued)

FOREIGN PATENT DOCUMENTS

| WO | 0021537 A | 4/2000 |
| WO | 2004100891 A2 | 11/2004 |

(Continued)

OTHER PUBLICATIONS

Antony et al., Molecular Pharmacology, 67: 523-530.*
Cancer and Metastasis Reviews (1998), 17(1), 91-106.*
Science (1999), vol. 286, 531-537.*
Arpicco et al., Anticancer Prodrugs: An Overview of Major Strategies and Recent Developments, Current topics in medical chemistry, Jun. 2011, pp. 2345-2381.
Cinelli et al., Identification, Sythesis, and Biological Evaluation of Metabolites of the Experimental Cancer Treatment Drugs Indotecan (LMP400) and Indimitecan (LMP776) and Investigation of Isomerically Hydroxylated Indenoisoquinoline Analogues as Topoisomerase I Poisons, Journal of Medicinal Chemistry, 2012, pp. 10844-10862, American Chemical Society.

(Continued)

*Primary Examiner* — Rebecca L Anderson
(74) *Attorney, Agent, or Firm* — Brannon Sowers & Cracraft

(57) ABSTRACT

Tyrosyl-DNA Phosphodiesterases 1 and 2 (Tdp1 and Tdp2) can repair damaged DNA resulting from topoisomerase inhibitors (e.g. Top1) and a variety of other DNA-damaging agents. 7-Azaindenoisoquinolines that are inhibitors of each of Top1, Tdp1 and Tdp2 are disclosed. Also described are methods for preparing azaindenoisoquinoline and methods for treating patients of a cancer using the disclosed azaindenoisoquinoline compounds or a pharmaceutical formulation thereof.

9 Claims, No Drawings

(56) References Cited

U.S. PATENT DOCUMENTS

| | | |
|---|---|---|
| 2014/0018360 A1 | 1/2014 | Cushman et al. |
| 2014/0187547 A1 | 7/2014 | Cushman et al. |
| 2014/0336188 A1 | 11/2014 | Cushman et al. |
| 2015/0133445 A1 | 5/2015 | Cushman et al. |
| 2015/0148370 A1 | 5/2015 | Cushman et al. |
| 2015/0210686 A1 | 7/2015 | Dorsch et al. |
| 2015/0218207 A1 | 8/2015 | Cushman et al. |
| 2015/0299246 A1 | 10/2015 | Cushman et al. |
| 2016/0081999 A1 | 3/2016 | Cushman et al. |
| 2016/0229888 A1 | 8/2016 | Cushman et al. |
| 2016/0318946 A1 | 11/2016 | Cushman et al. |

FOREIGN PATENT DOCUMENTS

| | | |
|---|---|---|
| WO | 2005089294 A2 | 9/2005 |
| WO | 2007059008 A2 | 5/2007 |
| WO | 2008076767 A1 | 6/2008 |
| WO | 2009140467 A1 | 11/2009 |
| WO | 2011094416 A1 | 8/2011 |
| WO | 2012024437 A1 | 2/2012 |
| WO | 2012162513 A2 | 11/2012 |
| WO | 2015069766 A1 | 5/2015 |

OTHER PUBLICATIONS

Staker et al., Structures of Three Classes of Anticancer Agents Bound to the Human Topoisomerase I—DNA Covalent Complex, Journal of Medicinal Chemistry, 2005, pp. 2336-2345, American Chemical Society.

Staker, Bart L. et al., The Mechanism of Topoisomerase I Poisoning by a Campthothecin Analog, Proc. Natl. Acad. Sci, 2002, pp. 15387-15392, vol. 99, No. 24.

Wall, Monroe E., et al., Bifunctional Reagents, Cross-linking of Pancreatic Ribonuclease With a Diimido Ester, J. Am. Chem. Soc., 1966, pp. 3888-3890, vol. 88, No. 16.

Paull, K. D. et al., Display and Analysis of Patterns of Differential Activity of Drugs Against Human Tumor Cell Lines: Development of Mean Graph and COMPARE Algorithm, J. Natl. Cancer Inst., Jul. 19, 1989, pp. 1088-1091, vol. 81, No. 14.

Teicher, Beverly A., Next Generation Topoisomerase I Inhibitors: Rationale and Biomarker Strategies, Biochem. Pharmacology, 2008, pp. 1262-1271, vol. 75, Elsevier Inc.

Thomas, Craig J. et al., Camptothecin: Current Perspectives, Bioorganic & Medicinal Chemistry, 2004, pp. 1585-1604, vol. 12, Science Direct.

Pommier, Yves et al., DNA Topoisomerases and Their Poisoning by Anticancer and Antibacterial Drugs, Chemistry & Biology, May 28, 2010, pp. 421-433, vol. 17, Elsevier Ltd.

Stella, Valentino J., Prodrugs As Therapeutics, Expert Opinion on Therapeutic Patents, 2004, pp. 277-280, vol. 14, No. 3, Taylor & Francis.

Testa, Bernard, Prodrug Research: Futile or Fertile?, Biochemical Pharmacology, 2004, pp. 2097-2106, vol. 68, Science Direct.

Rautio, Jarkko et al., Prodrugs: Design and Clinical Applications, Nature Reviews Drug Discovery, Mar. 2008, pp. 255-270, vol. 7, Nature Publishing Group.

International Search Report, PCT/US17/16331, dated Apr. 28, 2017.

Jung "Prednisolone 21-sulfate sodium: a colon-specific pro-drug of prednisolone" 2003, 55, 1075-1082.

International Search Report, PCT/US2017/067206, dated Apr. 24, 2018.

International Search Report, PCT/US2017/022389, dated Jun. 9, 2017.

Kiselev et al. "Optimization of the Lactam Side Chain of 7-Azaindenoisoquinoline Topoisomerase I Inhibitors and Mechanism of Action Studies in Cancer Cells" Journal of Medicinal Chemistry. Feb. 6, 2014 (Feb. 6, 2014) vol. 57, p. 1289-1298; p. 1290.

Beck et al. 'Discovery of Potent Indenoisoquinoline Topoisomerase I Poisons Lacking the Nitro Toxicophore', Journal of medicinal chemistry, 2015, vol. 58.9, pp. 3997-4015. p. 3997, col. 1, para 2; p. 3998, col. 1, para 1; p. 4001, Scheme 8; p. 4003, Table 2.

Kiselev, Evgeny, et al. "7-azaindenoisoquinolines as topoisomerase I inhibitors and potential anticancer agents." Journal of medicinal chemistry 54.17 (2011): 6106-6116.

Kiselev, Evgeny, et al. "Azaindenoisoquinolines as topoisomerase I inhibitors and potential anticancer agents: a systematic study of structure-activity relationships." Journal of medicinal chemistry 55.4 (2012): 1682-1697.

Kiselev, Evgeny, et al. "Optimization of the lactam side chain of 7-azaindenoisoquinoline topoisomerase I inhibitors and mechanism of action studies in cancer cells." Journal of medicinal chemistry 57.4 (2014): 1289-1298.

Wang, Ping, et al. "Synthesis and biological evaluation of the first triple inhibitors of human topoisomerase 1, tyrosyl-DNA phosphodiesterase 1 (Tdp1), and tyrosyl-DNA phosphodiesterase 2 (Tdp2)." Journal of medicinal chemistry 60.8 (2017): 3275-3288.

Elsayed, Mohamed SA, et al. "Design and synthesis of chlorinated and fluorinated 7-azaindenoisoquinolines as potent cytotoxic anti-cancer agents that inhibit topoisomerase I." Journal of medicinal chemistry 60.13 (2017): 5364-5376.

Beck, Daniel E., et al. "Investigation of the Structure-Activity Relationships of Aza—A-Ring Indenoisoquinoline Topoisomerase I Poisons." Journal of medicinal chemistry 59.8 (2016): 3840-3853.

Beck Daniel E et al: "Synthesis and biological evaluation of new fluorinated and chlorinated indenoisoquinoline topoisomerase I poisons", Bioorganic & Medicinal Chemistry, vol. 24, No. 7, Feb. 9, 2016, pp. 1469-1479, XP029459043.

\* cited by examiner

AZAINDENOISOQUINOLINE COMPOUNDS AND USES THEREOF

CROSS-REFERENCE TO RELATED APPLICATIONS

This application is a national application under 37 C.F.R § 371(b) of International Application No. PCT/US2017/067206, filed Dec. 19, 2017, which claims the benefit of U.S. Provisional Patent Application No. 62/437,777, filed Dec. 22, 2016, the contents of each of which are hereby incorporated by reference in their entirety into this disclosure.

GOVERNMENT RIGHTS

This invention was made with government support under CA023168, awarded by the National Institutes of Health. The United States government has certain rights in the invention.

TECHNICAL FIELD

The present disclosure generally relates to novel compounds for a variety of therapeutic uses. In particular, this disclosure relates to azaindenoisoquinoline compounds as triple inhibitors of Topoisomerase 1 (Top1), and Tyrosyl-DNA Phosphodiesterases 1 and 2 (Tdp1 and Tdp2) that are useful for treatment of a cancer.

BACKGROUNDS

This section introduces aspects that may help facilitate a better understanding of the disclosure. Accordingly, these statements are to be read in this light and are not to be understood as admissions about what is or is not prior art.

Cancer is a group of diseases involving abnormal cell growth with the potential to invade or spread to other parts of the body. There are more than 100 types of cancer that affect human beings. In 2016, there were an estimated 1,685,210 new cancer cases diagnosed and 595,690 cancer deaths in the U.S. alone (*Cancer Statistics* 2016—American Cancer Society, Inc.). There are unmet and increasing needs for new and novel therapies for fighting cancers.

The inhibition of DNA topoisomerase I (Top1) has proven to be a successful approach to the design of anticancer agents. Camptothecins (CPTs) and indenoisoquinolines are two established classes of Top1 inhibitors (Staker, et al., *J. Med. Chem.* 2005, 48, 2336-2345; Pommier, et al, *Mol. Cancer Ther.* 2009, 8, 1008-1014)). The CPTs and indenoisoquinolines act through stabilization of the DNA-Top1 covalent cleavage complex (Top1cc) by a dual DNA intercalation and protein binding mechanism that leads to inhibition of the DNA re-ligation process (Pmmier, et al., *Nat. Rev. Drug Discovery* 2012, 11, 25-36). Subsequent collision of the DNA replication fork with drug-stabilized complexes causes DNA double-stranded breaks. Ultimately, this leads to tumor cell death. DNA repair after Top1-mediated DNA cleavage is a complex process that can be initiated by tyrosyl-DNA phosphodiesterase 1 (Tdp1) (Plo, et al., *DNA Repair* 2003, 2, 1087-1100; Davies, et al., *J. Mol. Biol.* 2002, 324, 917-932), which plays a critical role in development of drug resistance (Perego, et al., *Biochem. Pharmacol.* 2012, 83, 27-36). Tdp1 is a member of the phospholipase D superfamily of enzymes that catalyze the hydrolysis of the 3'-phosphotyrosyl linker found in the Top1cc and other 3'-end DNA blocking lesions (Interthal, et al., *Proc. Natl. Acad. Sci. U.S.A.* 2001, 98, 12009-12014; Murai, et al., *J. Biol. Chem.* 2012, 287, 12848-12857).

On the other hand, tyrosyl-DNA phosphodiesterase II (Tdp2) is a member of the metal-dependent phosphodiesterases that was recently discovered with repair function linked to topoisomerase II (Top2)-mediated DNA damage (Pommier, et al., *DNA Repair* 2014, 19, 114-129). Tdp2 cleaves Top2-DNA adducts by catalyzing the hydrolysis of 5'-phosphotyrosyl bonds and thereby releasing trapped Top2 from 5'-termini, thus playing a key role in maintaining normal DNA topology. Inhibition of Tdp2 may therefore be a useful approach to overcome intrinsic or acquired resistance to Top2-targeted drug therapy (Zeng, et al., *J. Biol. Chem.* 2011, 286, 403-409; Ledesma, et al., *Nature,* 2009, 461, 674). More recently, it was revealed that Tdp2 also promotes repair of Top1-mediated DNA damage in the absence of Tdp1 and that cells lacking both Tdp1 and Tdp2 are more sensitive to Top1 inhibitors than Tdp1-deficient cells (Maede, et al., *Mol. Cancer Ther.* 2014, 13, 214-220). The hypothesis that Tdp2 may serve as a potential therapeutic co-target of Top1 and Tdp1 needs to be investigated (Pommier, et al., 2014; Zeng, et al., 2011).

BRIEF SUMMARY OF INVENTION

Described herein are azaindenoisoquinoline compounds. The compounds described herein may be useful for treating a cancer. In particular those azaindenoisoquinoline compounds may be useful as triple inhibitors of Topoisomerase 1 (Top1), and Tyrosyl-DNA Phosphodiesterases 1 and 2 (Tdp1 and Tdp2) that are useful for treatment of a cancer.

Also described herein are pharmaceutical compositions of such compounds and methods for treating cancer by administering therapeutically effective amounts of such compound alone or in pharmaceutical compositions.

In some illustrative embodiments, described herein are azaindenoisoquinoline compounds having the formula (I)

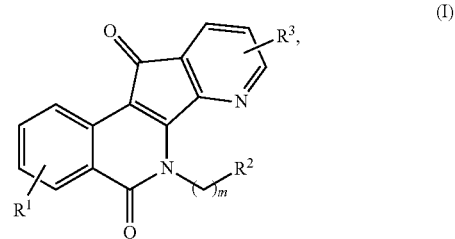

(I)

or a pharmaceutically acceptable salt thereof, wherein:
  m is an integer from 1 to about 6;
  $R^1$ represents 1-4 substituents each of which is independently selected from the group consisting of hydrogen, halo, hydroxy, nitro, cyano, optionally substituted alkyl, optionally substituted alkoxy, optionally substituted alkylthio, optionally substituted alkylsulfonyl, carboxylic acid, and sulfonic acid; or $R^1$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid;

$R^2$ is selected from the group consisting of heteroaryl, heteroaryloxy, heteroarylamino, heteroarylalkylaminoalkylamino, heterocyclyl, heterocyclylamino, amino, hydroxyl, halo, cyano, alkylamino, dialkylamino, trialkylammonium, bis(hydroxyalkyl)amino, and hydroxyalkylaminoalkylamino, wherein each of heteroaryl, heteroaryloxy, and heteroarylamino, heteroarylalkylaminoalkylamino, heterocyclyl, and heterocyclylamino is optionally substituted; and $R^3$ represents 1-3 substituents each of which is independently selected from the group consisting of hydrogen, halo, hydroxy, cyano, nitro, optionally substituted alkyl, optionally substituted alkoxy, optionally substituted alkylthio, optionally substituted alkylsulfonyl, carboxylic acid, and sulfonic acid; or $R^3$ represents 2-3 substituents where 2 of said substituents are adjacent substituents and are taken together with the attached carbons to form an optionally substituted heterocycle, and where the remaining substituent is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid, and wherein at least one of $R^1$ or $R^3$ is not hydrogen.

In some other embodiments, described herein are azaindenoisoquinoline compounds having the formula (I), wherein $R^2$ is a substituent selected from the group consisting of:

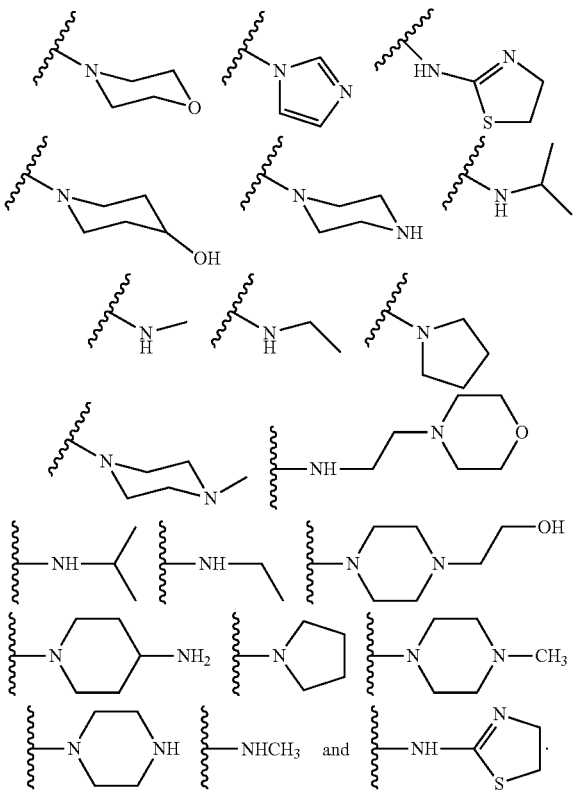

In some illustrative embodiments, described herein is a pharmaceutical composition comprising a compound having the formula (I), or a pharmaceutically acceptable salt, hydrate, or solvate thereof, and a pharmaceutically acceptable carrier, diluent, and excipient.

In some other illustrative embodiments, described herein is a method for treating a patient with a cancer, the method comprising the step of administering a therapeutically effective amount of a compound having the formula (I), or a pharmaceutically acceptable salt thereof, and a pharmaceutically acceptable carrier, diluent, and excipient to the patient in need of relief from said cancer.

In some other illustrative embodiments, described herein are substances for treating a patient with a cancer, the substance having the formula (I), or a pharmaceutically acceptable salt thereof, together with a pharmaceutically acceptable carrier, diluent, and excipient to the patient in need of relief from said cancer.

In some embodiments, pharmaceutical compositions containing one or more of the compounds are also described herein. In one aspect, the compositions include a therapeutically effective amount of the one or more compounds for treating a cancer patient. It is to be understood that the compositions may include other component and/or ingredients, including, but not limited to, other therapeutically active compounds, and/or one or more pharmaceutically acceptable carriers, diluents, excipients, and the like.

It is appreciated herein that the compounds described herein may be used alone or in combination with other compounds useful for treating cancer, including those compounds that may be therapeutically effective by the same or different modes of action. In addition, it is appreciated herein that the compounds described herein may be used in combination with other compounds that are administered to treat other symptoms of cancer, such as compounds administered to relieve nausea, vomiting, pain, osteoporosis, and the like.

DETAILED DESCRIPTION

For the purposes of promoting an understanding of the principles of the present disclosure, references will now be made to the embodiments illustrated in the drawings, and specific language will be used to describe the same. It will nevertheless be understood that no limitation of the scope of this disclosure is thereby intended.

As used herein, the following terms and phrases shall have the meanings set forth below. Unless defined otherwise, all technical and scientific terms used herein have the same meaning as commonly understood to one of ordinary skill in the art.

A "halogen" designates F, Cl, Br or I. A "halogen-substitution" or "halo" substitution designates replacement of one or more hydrogen atoms with F, Cl, Br or I.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$ alkyl, methyl, ethyl, propyl, 3-methylpentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, and the like.

As used herein, the term "alkynyl" refers to an unsaturated monovalent chain of carbon atoms including at least one triple bond, which may be optionally branched. It is understood that in embodiments that include alkynyl, illustrative variations of those embodiments include lower alkynyl, such as $C_2$-$C_6$, $C_2$-$C_4$ alkynyl, and the like.

As used herein, the term "cycloalkyl" refers to a monovalent chain of carbon atoms, a portion of which forms a ring. It is understood that in embodiments that include cycloalkyl, illustrative variations of those embodiments include lower cycloalkyl, such as $C_3$-$C_8$ cycloalkyl, cyclopropyl, cyclohexyl, 3-ethylcyclopentyl, and the like.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as $C_2$-$C_4$, alkylene, methylene, ethylene, propylene, 3-methylpentylene, and the like.

As used herein, the term "heterocyclic" or "heterocycle" refers to a monovalent chain of carbon and heteroatoms, wherein the heteroatoms are selected from nitrogen, oxygen, and sulfur, and a portion of which, at least one heteroatom, forms a ring. The term "heterocycle" may include both "aromatic heterocycles" and "non-aromatic heterocycles." Heterocycles include 4-7 membered monocyclic and 8-12 membered bicyclic rings, such as imidazolyl, thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, azetidinyl, oxetanyl, thiiranyl, oxiranyl, aziridinyl, and the like. "Heterocycles" may be optionally substituted at any one or more positions capable of bearing a hydrogen atom.

As used herein, the term "aryl" includes monocyclic and polycyclic aromatic carbocyclic groups, each of which may be optionally substituted. The term "optionally substituted aryl" refers to an aromatic mono or polycyclic ring of carbon atoms, such as phenyl, naphthyl, and the like, which may be optionally substituted with one or more independently selected substituents, such as halo, hydroxyl, amino, alkyl, or alkoxy, alkylsulfony, cyano, nitro, and the like.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" may also include ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocycle. Heteroaryl groups include, for example, pyrrole, furan, thiophene, imidazole, oxazole, thiazole, pyrazole, pyridine, pyrazine, pyridazine, and pyrimidine.

It is understood that each of alkyl, cycloalkyl, alkenyl, cycloalkenyl, alkylene, and heterocycle may be optionally substituted with independently selected groups such as alkyl, haloalkyl, hydroxyalkyl, aminoalkyl, carboxylic acid and derivatives thereof, including esters, amides, and nitrites, hydroxy, alkoxy, acyloxy, amino, alky and dialkylamino, acylamino, thio, and the like, and combinations thereof.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structure, and upon such occurrence each term shall be defined independently of the other.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

It is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosage may be single or divided, and may be administered according to a wide variety of dosing protocols, including q.d., b.i.d., t.i.d., or even every other day, once a week, once a month, and the like. In each case the therapeutically effective amount described herein corresponds to the instance of administration, or alternatively to the total daily, weekly, or monthly dose.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., *Cancer Chemother. Rep.* 1966, 50 (4), 219, the disclosure of which is incorporated herein by reference. Body surface area may be approximately determined from patient height and weight (see, e.g., Scientific Tables 1970, Geigy Pharmaceuticals, Ardley, N.Y., pages 537-538). A therapeutically effective amount of the compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of compound per patient body weight. It is appreciated that effective doses may also vary depending on the route of administration, optional excipient usage, and the possibility of co-usage of the compound with other conventional and non-conventional therapeutic treatments, including other anti-tumor agents, radiation therapy, and the like.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, or within 99% of a stated value or of a stated limit of a range.

In some illustrative embodiments, the present invention relates to azaindenoisoquinoline compounds having the formula (I)

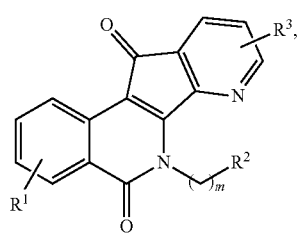

or a pharmaceutically acceptable salt thereof, wherein:
m is an integer from 1 to about 6;
$R^1$ represents 1-4 substituents each of which is independently selected from the group consisting of hydrogen, halo, hydroxy, nitro, cyano, optionally substituted alkyl, optionally substituted alkoxy, optionally substituted alkylthio, optionally substituted alkylsulfonyl, carboxylic acid, and sulfonic acid; or $R^1$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid;
$R^2$ is selected from the group consisting of heteroaryl, heteroaryloxy, heteroarylamino, heteroarylalkylaminoalkylamino, heterocyclyl, heterocyclylamino, amino, hydroxyl, halo, cyano, alkylamino, dialkylamino, trialkylammonium, bis(hydroxyalkyl)amino, and hydroxyalkylaminoalkylamino, wherein each of heteroaryl, heteroaryloxy, and heteroarylamino, heteroarylalkylaminoalkylamino, heterocyclyl, and heterocyclylamino is optionally substituted; and
$R^3$ represents 1-3 substituents each of which is independently selected from the group consisting of hydrogen, halo, hydroxy, cyano, nitro, optionally substituted alkyl, optionally substituted alkoxy, optionally substituted alkylthio, optionally substituted alkylsulfonyl, carboxylic acid, and sulfonic acid; or $R^3$ represents 2-3 substituents where 2 of said substituents are adjacent substituents and are taken together with the attached carbons to form an optionally substituted heterocycle, and where the remaining substituent is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid, and wherein at least one of $R^1$ or $R^3$ is not hydrogen.

In some other embodiments, the present invention relates to azaindenoisoquinoline compounds having the formula (I), wherein one of $R^1$ is chloro or fluoro and the remaining substituents are hydrogen.

In some other embodiments, the present invention relates to azaindenoisoquinoline compounds having the formula (I), wherein one of $R^1$ is nitro and the remaining substituents are hydrogen.

In some other embodiments, the present invention relates to azaindenoisoquinoline compounds having the formula (I), wherein $R^2$ is a halo or cyano.

In some other embodiments, the present invention related to azaindenoisoquinoline compounds having the formula (I), wherein $R^2$ is a substituent selected from the group consisting of:

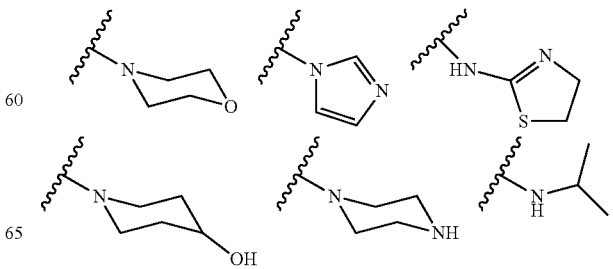

-continued

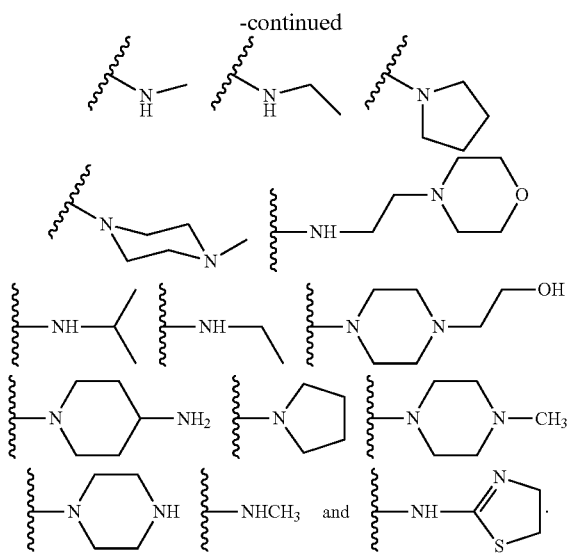

In some illustrative embodiments, described herein are azaindenoisoquinoline compounds having the formula (II)

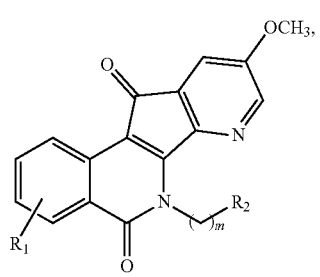

(II)

or a pharmaceutically acceptable salt thereof, wherein:
m is an integer from 1 to about 6;
$R^1$ represents 1-4 substituents each of which is independently selected from the group consisting of hydrogen, halo, hydroxy, nitro, cyano, optionally substituted alkyl, optionally substituted alkoxy, optionally substituted alkylthio, optionally substituted alkylsulfonyl, carboxylic acid, and sulfonic acid; or $R^1$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid; and
$R^2$ is selected from the group consisting of heteroaryl, heteroaryloxy, heteroarylamino, heteroarylalkylaminoalkylamino, heterocyclyl, heterocyclylamino, amino, hydroxyl, halo, cyano, alkylamino, dialkylamino, trialkylammonium, bis(hydroxyalkyl)amino, and hydroxyalkylaminoalkylamino, wherein each of heteroaryl, heteroaryloxy, and heteroarylamino, heteroarylalkylaminoalkylamino, heterocyclyl, and heterocyclylamino is optionally substituted;

In some other embodiments, the present invention relates to azaindenoisoquinoline compounds having the formula (II), wherein one of $R^1$ is chloro or fluoro and the remaining substituents are hydrogen.

In some other embodiments, the present invention relates to azaindenoisoquinoline compounds having the formula (II), wherein one of $R^1$ is nitro and the remaining substituents are hydrogen.

In some other embodiments, the present invention relates to azaindenoisoquinoline compounds having the formula (II), wherein $R^2$ is a halo or cyano.

In some other embodiments, the present invention related to azaindenoisoquinoline compounds having the formula (II), wherein $R^2$ is a substituent selected from the group consisting of:

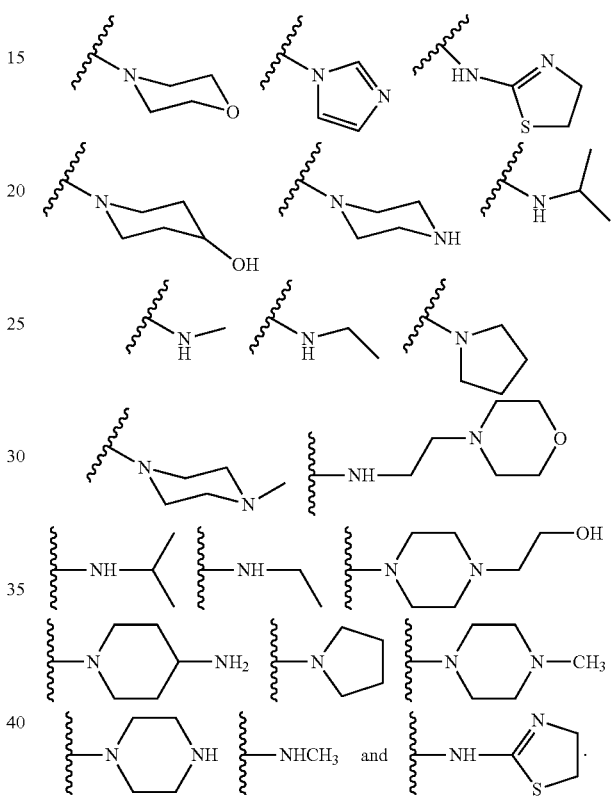

In some other embodiments, the present invention relates to azaindenoisoquinoline compounds having the formula (I), wherein one of $R^3$ is an alkoxy and the remaining $R^3$ substituents are hydrogen.

In some other embodiments, the present invention relates to azaindenoisoquinoline compounds having the formula (II), wherein one of $R^3$ is alkoxy and the remaining $R^3$ substituents are hydrogen.

In some other embodiments, the present invention relates a pharmaceutical composition comprising a compound of formula (I), or a pharmaceutically acceptable salt thereof, and one or more pharmaceutically acceptable carriers, diluents, and excipients.

In some other embodiments, the present invention relates a pharmaceutical composition comprising a compound of formula (II), or a pharmaceutically acceptable salt thereof, and one or more pharmaceutically acceptable carriers, diluents, and excipients.

In some other embodiments, the present invention relates a method for treating a patient with a cancer, comprising the step of administering a therapeutically effective amount of the pharmaceutical composition disclosed herein to the patient in need of relief from said cancer.

In some other embodiments, the present invention relates a method for treating a patient with a cancer, the method comprising the step of administering a therapeutically effective amount of a compound disclosed herein, together with one or more pharmaceutically acceptable carriers, diluents, and excipients, to the patient in need of relief from said cancer.

In some other embodiments, the present invention relates a method for treating a patient with a cancer, the method comprising the step of administering a therapeutically effective amount of a compound disclosed herein, and a therapeutically effective amount of one or more other compounds of the same or different mode of action, together one or more pharmaceutically acceptable carriers, diluents, and excipients, to the patient in need of relief from said cancer.

In some embodiments, the present invention relates a method for treating a patient with a cancer, the method comprising the step of administering a therapeutically effective amount of a compound functioning as a triple inhibitor toward human topoisomerase 1, tyrosyl-DNA phosphodiesterase 1, and tyrosyl-DNA phosphodiesterase 2.

In some other embodiments, the present invention relates a substance for use in the treatment of a cancer, the substance having formula (I)

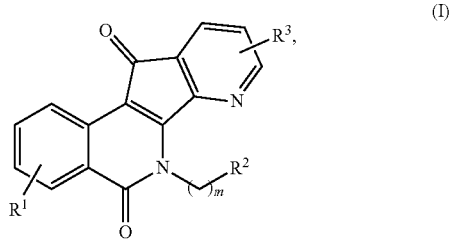

or a pharmaceutically acceptable salt thereof, wherein:
m is an integer from 1 to about 6;
$R^1$ represents 1-4 substituents each of which is independently selected from the group consisting of hydrogen, halo, hydroxy, nitro, cyano, optionally substituted alkyl, optionally substituted alkoxy, optionally substituted alkylthio, optionally substituted alkylsulfonyl, carboxylic acid, and sulfonic acid; or $R^1$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid;
$R^2$ is selected from the group consisting of heteroaryl, heteroaryloxy, heteroarylamino, heteroarylalkylaminoalkylamino, heterocyclyl, heterocyclylamino, amino, hydroxyl, halo, cyano, alkylamino, dialkylamino, trialkylammonium, bis(hydroxyalkyl)amino, and hydroxyalkylaminoalkylamino, wherein each of heteroaryl, heteroaryloxy, and heteroarylamino, heteroarylalkylaminoalkylamino, heterocyclyl, and heterocyclylamino is optionally substituted; and
$R^3$ represents 1-3 substituents each of which is independently selected from the group consisting of hydrogen, halo, hydroxy, cyano, nitro, optionally substituted alkyl, optionally substituted alkoxy, optionally substituted alkylthio, optionally substituted alkylsulfonyl, carboxylic acid, and sulfonic acid; or $R^3$ represents 2-3 substituents where 2 of said substituents are adjacent substituents and are taken together with the attached carbons to form an optionally substituted heterocycle, and where the remaining substituent is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid, and sulfonic acid, and wherein at least one of $R^1$ or $R^3$ is not hydrogen.

The present invention may be better understood in light of the following non-limiting compound examples and method examples.

Preparation of compound 7 was first explored through Mitsunobu reaction by treating 6 (Kiselev, et al, *J. Med. Chem.* 2012, 55, 1682-1697) with 3-bromopropanol, Ph$_3$P, and DIAD in THF (Scheme 1), but only a moderate yield (39%) was obtained and tedious chromatography was required to get pure product. An S$_N$2 substitution with 1,3-dibromopropane was then investigated to install the 3-bromopropyl side chain. After thorough optimization of the reaction conditions, it was determined that when compound 6 was treated with sodium hydride in anhydrous DMF, followed by addition of sodium iodide (0.1 equiv) and 1,3-dibromopropane at −10° C. to 0° C. for 30 hours, compound 7 could be obtained in 72% yield. This improvement in yield over the previously reported reaction conditions resulted from the use of NaI (Kiselev, et al, *J. Med. Chem.* 2014, 57, 1289-1298). The practical preparation of compound 7 on a gram scale made it possible to synthesize 7-azaindenoisoquinoline analogues with maximum side chain variation, thereby facilitating the structure-activity relationship (SAR) study.

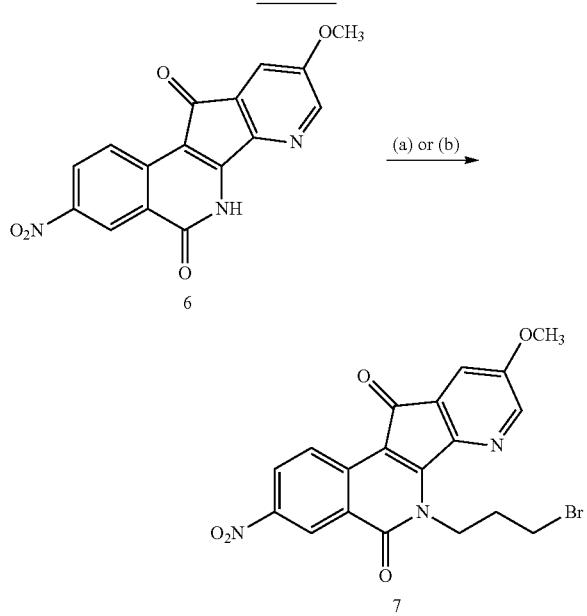

[a] Reagents and conditions: (a) 3-bromopropanol, triphenylphosphine, DIAD, THF, 23° C., 60 h, 39%; (b) i) NaH, DMF, 0° C. to 23° C., 3 h; ii) 1,3-dibromopropane, 0.1 equiv NaI, -10 to 0° C., 30 h, 72%.

Scheme 2[a]

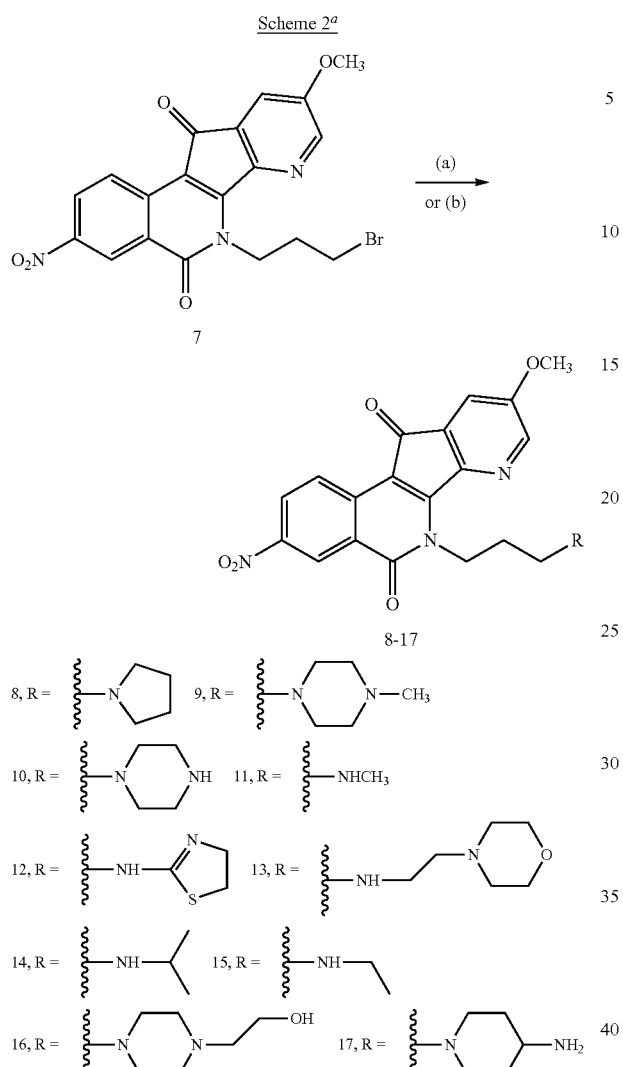

[a]Reagents and conditions: (a) amine (pyrrolidine for 8, 1-methylpiperazine for 9, piperazine for 10, 2-amino-2-thiazoline for 12, and 4-(2-aminoethyl)morpholine for 13, 1-(2-hydroxyethyl)piperazine for 16, and 4-aminopiperidine for 17), NaI, K$_2$CO$_3$, 1,4-dioxane, reflux, 6 h (8, 68%; 9, 77%; 10, 66%; 12, 57%; 13, 50%; 16, 53%, 17, 63%, or (b) amine (methylamine for 11, isopropylamine for 14, ethylamine for 15, NaI, Et$_3$N, DMF, room temperature, 12 h (11, 68%; 14, 80%; 15, 73%).

promoted by Et$_3$N afforded compounds 13a-b in ~25% yield for two steps. Oxidation of 13a-b with selenium dioxide provided azaindenoisoquinoline intermediates 14a-b. Treating compounds 14a-b with NaH in DMF at 0° C. followed by reaction with 1-chloro-3-bromopropane yielded the common intermediates 15a-b. The common intermediates 15a-b were used for the synthesis of the final compounds 16a-j and 17a-i by alkylation of the corresponding amines in DMF as shown in Scheme 4.

Scheme 3

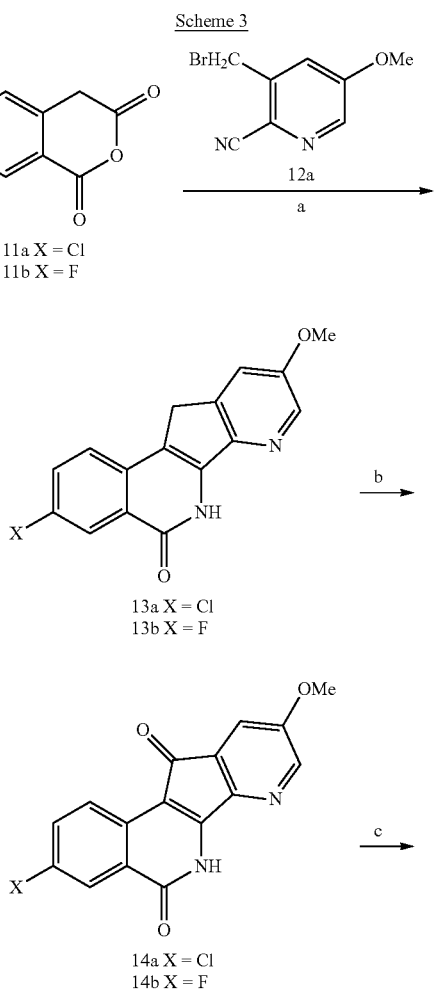

The SAR study was restricted to varying the lactam γ-aminopropyl side chain. As illustrated in Scheme 2, compounds 8, 9, 10, 12, 13, 16 and 17 were prepared in 50-77% yields by heating compound 7 with the corresponding amines at reflux in 1,4-dioxane in the presence of K$_2$CO$_3$ and NaI, while compounds 11, 14 and 15 were obtained by treatment of 7 with methylamine, isopropylamine, and ethylamine in DMF at room temperature in the presence of triethylamine and 0.1 equivalent of NaI in 68%, 80% and 73% yields, respectively.

The anhydrides 11a and 11b (Scheme 3) were prepared by published literature procedures (Kang, B.-R, et al., Med. Chem. Res. 2014, 23, 1340-1349). Bromination of 5-methoxy-3-methylpicolinonitrile in the presence of the radical initiator AIBN produced intermediate bromide 12a (Kiselev, et al, J. Med. Chem. 2011, 54, 6106-6116), which was used directly in the next step without additional purification. The condensation of 12a and 11a-b in acetonitrile Reagents and conditions: (a) Et$_3$N, CH$_3$CN, reflux, 24 h, 25% for two steps; (b) SeO$_2$, 1-4-dioxane, reflux, 24 H, 86%; (c) i, NaH, DMF, 0° C. to RT, 3 h; ii) 1-bromo-3-chloropropane, -10-0° C., 24 h, 78%.

Scheme 4

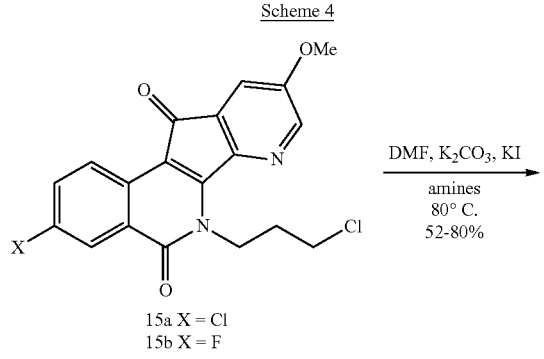

15a X = Cl
15b X = F

DMF, K₂CO₃, KI
amines
80° C.
52-80%

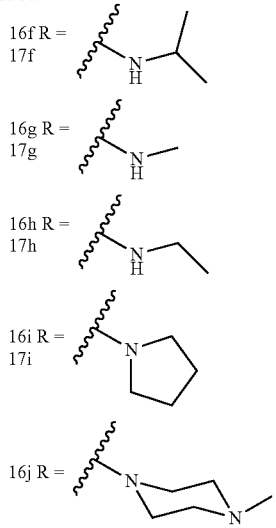

16f R =
17f

16g R =
17g

16h R =
17h

16i R =
17i

16j R =
17j

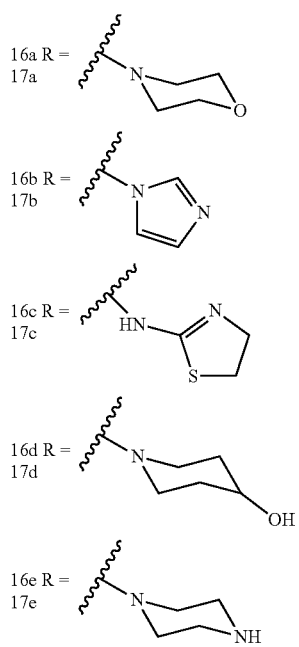

16a R =
17a

16b R =
17b

16c R =
17c

16d R =
17d

16e R =
17e

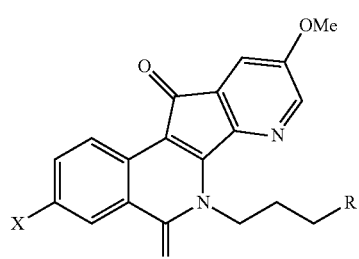

16 series X = Cl
17 series X = F

Biological Results and Discussion

All of the synthesized compounds 7-17 were tested for their inhibitory activities against Top1, Tdp1, and Tdp2. Their antiproliferative activities were also evaluated against the NCI-60 panel of human cancer cell lines. Top1 inhibition was recorded as the ability of the drug to induce enzyme-linked DNA breaks in the Top1-mediated DNA cleavage assay (Dexheimer, et al., *Nat. Protoc.* 2008, 3, 1736-1750). The results of this assay are designated relative to the Top1 inhibitory activities of camptothecin (18) and MJ-III-65 (19) (also known as NSC 706744 and LMP744, respectively) and are expressed in semi quantitative fashion: 0, no detectable activity; +, weak activity; ++, less activity than that of compound 19; +++, similar activity to that of 19; ++++, equipotent to 18. As shown in Table 1, all of the compounds 7-17 exhibited moderate to potent Top1 inhibitory activity. Compound 7 expressed Top1 inhibitory activity at the ++ potency level. Further evaluation of analogues with various amino groups in the side chain (pyrrolidine, 8; 1-methylpiperazine, 9; and piperazine, 10) revealed similar Top1 inhibitory activities at the ++ level. Interestingly, compound 11, in which a methylamine was introduced at the end of propyl chain, displayed improved Top inhibitory activity relative to 7 at the +++ level. Notably, the isopropylamine 14 and ethylamine 15 compounds demonstrated excellent Top1 inhibitory activity at the ++++ level. The 4-2(aminoethyl) morpholine compound 13 and 2-amino-2-thiazoline compound 12 displayed improved Top1 inhibitory activity relative to 7 at the +++ and ++++ levels, respectively. The improved potencies of compounds 11-15 compared to those of 8-10 indicate that a secondary amine in side chain of 7-azaindenoisoquinolines is better than a tertiary amine for the Top1 inhibitory activity.

The Tdp1 inhibitory activities of the 7-azaindenoisoquinolines were determining by measuring their abilities to inhibit the hydrolysis of the phosphodiester linkage between the tyrosine residue and the 3'-end of a DNA oligonucleotide substrate (N14Y), thus preventing the generation of an oligonucleotide with a free 3'-phosphate (N14P) (Dexheimer, et al., *J. Med. Chem.* 2009, 52, 7122-7131). The Tdp1 inhibitory activities of the 7-azaindenoisoquinolines are summarized in Table 1. Tdp1 inhibitory potencies were determined in duplicate using a semiquantitative scale: 0, $IC_{50}>111$ μM; +, $IC_{50}$ between 37 and 111 μM; ++, $IC_{50}$ between 12 and 37 μM; +++, $IC_{50}$ between 1 and 12 μM; and ++++, $IC_{50}<1$ μM.

TABLE 1

Top1, Tdp1, and Tdp2 inhibitory activities and cytotoxicities of 7-azaindenoisoquinolines (series 1)

| | Cytotoxicity (GI$_{50}$, μM)$^a$ | | | | | | | Enzyme Inhibitory Activity | | |
|---|---|---|---|---|---|---|---|---|---|---|
| | lung | CNS | Melanoma | Ovarian | Renal | Breast | | | | |
| Compd | HOP-62 | SF-539 | UACC-62 | OVCAR-3 | SN12C | MCF-7 | MGM | Top1$^c$ | Tdp1$^d$ | Tdp2$^d$ |
| 7 | 0.058 | 0.279 | 0.082 | 0.248 | 0.269 | 0.046 | 0.112 | ++ | ++ | + |
| 8 | <0.01 | 0.031 | 0.015 | 0.059 | 0.036 | <0.01 | 0.045 | ++ | +++ | + |
| 9 | 0.081 | 0.191 | 0.183 | 0.171 | 0.214 | 0.016 | 0.562 | ++ | ++ | ++ |
| 10 | 0.065 | 0.355 | 0.175 | 1.190 | 0.230 | 0.036 | 0.316 | ++ | ++ | + |
| 11 | 0.030 | 0.051 | 0.020 | 0.174 | 0.046 | 1.06 | 0.741 | +++ | +++ | + |
| 12 | 0.014 | 0.036 | <0.01 | 0.137 | <0.01 | <0.01 | 0.058 | ++++ | +++ | ++ |
| 13 | 0.150 | 0.311 | 0.044 | 0.315 | 0.080 | 0.032 | 0.177 | +++ | ++ | + |
| 14 | 0.085 | 0.051 | 0.019 | 0.082 | 0.039 | 0.012 | 0.058 | ++++ | ++ | + |
| 15 | 0.107 | 0.070 | 0.027 | 0.062 | 0.053 | 0.019 | 0.079 | ++++ | +++ | + |
| 16 | 2.76 | 1.70 | 1.22 | 1.46 | — | 0.142 | 1.66 | +++ | 0 | 0 |
| 17 | NS$^b$ | NS | NS | NS | NS | NS | NS | ++ | +++ | +++ |
| 18 | <0.01 | <0.01 | <0.01 | 0.22 | 0.020 | 0.013 | 0.040 | ++++ | 0 | 0 |
| 19 | 0.02 | 0.04 | 0.03 | 0.50 | <0.01 | <0.01 | 0.21 | ++++ | +/++ | +++ |

$^a$The cytotoxicity GI$_{50}$ values listed are the concentrations corresponding to 50% growth inhibition and are the result of single determinations;
$^b$Not selected for 5-concentration testing due to low potency in the initial 1-concentration test.
$^c$Compound-induced DNA cleavage resulting from Top1 inhibition is graded by the following semiquantitative scale relative to 1 μM MJ-III-65 (19) and 1 μM camptothecin (18): 0, no detectable activity; +, weak activity; ++, activity less than that of MJ-III-65 (19); +++, activity equal to that of 19; ++++, activity equipotent with 18.
$^d$Tdp1 and Tdp2 IC$_{50}$ values were determined in duplicate using a semiquantitative scale: 0, IC$_{50}$ > 111 μM; +, IC$_{50}$ between 37 and 111 μM; ++, IC$_{50}$ between 12 and 37 μM; +++, IC$_{50}$ between 1 and 12 μM; ++++, IC$_{50}$ < 1 μM.

TABLE 2

Top1, Tdp1, and Tdp2 inhibitory activities and cytotoxicities of 7-azaindenoisoquinolines (series 2)

| | Cytotoxicity (GI$_{50}$, μM)$^a$ | | | | | | | | | Enzyme Inhibitory Activity | | |
|---|---|---|---|---|---|---|---|---|---|---|---|---|
| | Lung | Colon | CNS | Melanoma | Ovarian | Renal | Prostate | Breast | | | | |
| Compd | HOP-62 | HCT-116 | SF-539 | UACC-62 | Ovcar-3 | SN12C | DU-145 | MCF-7 | MGM | Top1$^b$ | Tdp1$^c$ | Tdp2$^d$ |
| 16a | 0.27 | 0.16 | 0.23 | 0.18 | 0.78 | NA | 0.41 | 0.09 | 0.10 | +++ | >111 | >111 |
| 17a | 0.187 | 0.115 | 0.228 | 0.235 | 0.250 | 0.320 | 0.341 | 0.044 | 0.269 | +++ | >111 | >111 |
| 16b | 0.02 | 0.014 | 0.038 | 0.028 | 0.12 | NA | 0.043 | <0.01 | 0.063 | +++ | >111 | >111 |
| 17b | <0.01 | <0.01 | 0.024 | 0.016 | 0.043 | <0.01 | <0.01 | <0.01 | 0.033 | +++ | >111 | >111 |
| 16c | 0.042 | 0.35 | 0.47 | 0.095 | 1.3 | NA | 0.092 | 0.036 | 0.39 | ++ | 11.9 ± 3.9 | 32.9 ± 5.7 |
| 17c | 0.059 | 0.082 | 0.305 | 0.344 | 0.567 | 0.238 | 0.144 | 0.033 | 0.269 | ++ | >111 | 61.6 ± 14 |
| 16d | 0.094 | 0.098 | 0.43 | 0.19 | 1.42 | NA | 0.27 | 0.042 | 0.66 | ++++ | 14 ± 1 | >111 |
| 17d | 0.142 | 0.089 | 0.295 | 0.240 | 0.254 | 0.189 | 0.174 | 0.031 | 0.199 | + | >111 | >111 |
| 16e | 0.20 | 0.298 | 1.33 | 1.43 | 1.43 | 0.489 | 0.242 | 0.089 | 0.58 | + | 20.2 ± 3.7 | >111 |
| 17e | 0.066 | 0.091 | 0.532 | 1.26 | 0.335 | 0.080 | 0.062 | 0.034 | 0.218 | + | >111 | 107 ± 5.2 |
| 16f | 0.070 | 0.138 | 0.554 | 0.303 | 1.39 | 0.417 | 0.173 | 0.037 | 0.380 | ++ | 33.3 ± 4.2 | >111 |
| 17f | 0.107 | 0.093 | 0.248 | 0.271 | 0.190 | 0.164 | 0.210 | 0.031 | 0.165 | ++ | >111 | >111 |
| 16g | 0.220 | 0.550 | 0.730 | 0.574 | 1.41 | 1.18 | 0.331 | 0.046 | 0.60 | ++/+++ | 16 ± 3.2 | >111 |
| 17g | 0.142 | 0.143 | 0.368 | 0.608 | 0.263 | 0.211 | 0.202 | 0.034 | 0.245 | + | >111 | 108 ± 3 |
| 16h | 0.122 | 0.203 | 0.506 | 0.532 | 2.13 | 0.675 | 0.208 | <0.01 | 0.426 | ++/+++ | 22.2 ± 6.4 | >111 |
| 17h | 0.149 | 0.136 | 0.320 | 0.341 | 0.282 | 0.151 | 0.215 | 0.042 | 0.229 | ++ | >111 | 104 |
| 16i | 0.046 | 0.104 | 1.98 | 2.09 | 5.97 | 2.05 | 0.186 | 0.023 | 0.630 | ++ | 27.5 ± 0.6 | >111 |
| 17i | 0.212 | 0.153 | 0.360 | 0.471 | 0.307 | 0.241 | 0.211 | 0.048 | 0.288 | +++ | >111 | >111 |
| 16j | 0.950 | 0.980 | 2.15 | 1.81 | 15.1 | 10.2 | 3.18 | 0.487 | 2.95 | + | >111 | >111 |

$^a$The cytotoxicity GI$_{50}$ values listed are the concentrations corresponding to 50% growth inhibition and are the result of single determinations;
$^b$Compound-induced DNA cleavage resulting from Top1 inhibition is graded by the following semiquantitative scale relative to 1 μM MJ-III-65 (19) and 1 μM camptothecin (18): 0, no detectable activity; +, weak activity; ++, activity less than that of MJ-III-65 (19); +++, activity equal to that of 19; ++++, activity equipotent with 18 (see Table 1).
$^c$Tdp1 and Tdp2 IC$_{50}$ values were determined in duplicate.

To investigate their potential as anticancer agents, the 7-azaindenoisoquinolines 7-17 were evaluated in the National Cancer Institute's Developmental Therapeutics Program screen against 60 human cancer cell lines (the "NCI-60," Shoemaker, R. H. *Nat. Rev. Cancer* 2006, 6, 813-823). The GI$_{50}$ values obtained with selected cell lines, along with the mean graph midpoint (MGM) values, are summarized in Table 1. The MGM was based on a calculation of the average GI$_{50}$ for all of the cell lines tested in which GI$_{50}$ values below and above the test range (0.01 μM to 100 μM) were taken as the minimum (0.01 μM) and maximum (100 μM) drug concentrations used in the screening test. Many of these new compounds display significant potencies against various cell lines with GI$_{50}$ MGMs in the low micromolar to submicromolar range (0.045-1.66 μM). The Top1 ++++ compounds 12, 14, and 15 were among the most cytotoxic, with MGM values of 0.058, 0.058, and 0.079 μM, respectively. The differences in cytotoxicity among these three compounds are low despite clear differences in Tdp1 and Tdp2 inhibition, suggesting that Tdp1 and Tdp2 inhibition do not contribute significantly to the cytotoxicities of these compounds. The Top1 +++ compounds are 11 (MGM 0.714 μM), 13 (MGM 0.177 μM), and 16 (MGM 1.650 μM). On the basis of the Tdp1 and Tdp2 inhibitory potencies, 16 is expected to be the least potent, which it clearly is. However, one would expect 11 to be the most cytotoxic, and in fact 13 is the most cytotoxic of the three compounds. Among the Top1++ compounds, 7 (MGM 0.112 M), 8 (MGM 0.045 μM), 9 (MGM 0.562 μM), 10 (MGM 0.316 μM), and 17 (not tested due to low cytotoxicity in the one-concentration preliminary testing), 17 is expected to be the most cytotoxic on the basis of Tdp1 and Tdp2 inhibition, but it is actually the least cytotoxic. Based on their performance against Top1, Tdp1, and Tdp2, compounds 7 or 10 should be the least cytotoxic, but actually 17 is. On the other hand, compound 8 is surprisingly the most cytotoxic compound in the whole series despite having relatively moderate Top1 inhibitory activity. Overall, these triple inhibitors are very cytotoxic anticancer agents, but their relative cytotoxicities cannot be rationalized simply on the basis of their inhibitory activities vs. the three enzymes. Other factors that could contribute to the lack of agreement between the enzyme inhibitory activities and cytotoxicities of these 7-azaindenoisoquinoline include differences in cellular uptake, distribution within the cell, metabolism, efflux from the cell, off-target effects, and lack of sufficient potency vs. Tdp1 and Tdp2 to exert a significant synergistic effect.

Compounds 16a-j and 17a-i were tested in a Top1-mediated DNA cleavage assay to assess Top1 poisoning activity and the results were summarized in Table 2. In addition, those compounds were tested for anti-proliferative activity in the NCI-60 human tumor cell line screen. The Top1-mediated DNA cleavage assay scores the activity of Top poisons with a rubric based on the activity of 1 μM camptothecin. Test agents are incubated at 0.1, 1, 10, and 100 μM concentrations with a 3'-[$^{32}$P]-labeled double-stranded DNA fragment and Top1 enzyme. Top1 poisons bind to and trap Top1-DNA cleavage complexes. The DNA cleavage pattern is then documented by gel electrophoresis. Visual comparison of the lanes produced with 1 μM CPT indicates the activity of the new compounds. Finally, a semiquantitative score which ranges from 0 (no activity) to ++++(activity equal to that of 1 μM CPT) is used to describe the activity of the new compounds (see Table 2 caption for a complete description of the scoring rubric). The biological activities of the compounds are summarized in Table 2. The compounds have a good to moderate Top1 inhibitory activity. Of the nineteen compounds synthesized, compound 16d displayed the best activity with a score of ++++, while five other compounds exhibited good activity with a score of +++. On the other hand, five compounds showed weak activity with only a "+" score. Some of the compounds act as Top1 suppressors at high concentration, which likely results from the binding of the drug to the DNA at high drug concentration, making the DNA a poorer substrate for the cleavage reaction.

Compounds Examples

General.

NMR spectra were obtained at 300 or 500 ($^1$H) and 75 or 125 ($^{13}$C) MHz using Bruker ARX300 or Bruker DX-2 500 [QNP probe or multinuclear broadband observe (BBO) probe, respectively] spectrometers. Column chromatography was performed with 230-400 mesh silica gel. The melting points were determined using capillary tubes with a Mel-Temp apparatus and are uncorrected. IR spectra were obtained using a Perkin-Elmer 1600 series FTIR spectrometer on salt plates or as KBr pellets. ESI-MS analyses were recorded on a FinniganMAT LCQ Classic mass spectrometer. APCI-MS analyses were performed using an Agilent 6320 ion trap mass spectrometer. EI/CIMS analyses were obtained with a Hewlett-Packard Engine mass spectrometer. All mass spectral analyses were performed at the Campus-Wide Mass Spectrometry Center of Purdue University. HPLC analyses were carried out on a Waters 1525 binary HPLC pump/Waters 2487 dual λ absorbance detector system using a 5 μm C18 reverse phase column. All reported yields refer to pure isolated compounds. Chemicals and solvents were of reagent grade and used as obtained from commercial sources without further purification. The purities of all of the biologically tested compounds were >95% as estimated by HPLC or determined by elemental analysis. For HPLC, the peak area of the major product was >95% of the combined total peak areas when monitored by a UV detector at 254 nm.

7-Aza-6-(3-bromopropyl)-5,6-dihydro-9-methoxy-3-nitro-5,11-dioxo-11H-indeno[1,2-c]isoquinoline (7)

(Kiselev, et al., *J. Med. Chem.* 2014, 57, 1289-1298). Sodium hydride (234 mg, 9.28 mmol) and sodium iodide (70 mg, 0.464 mmol) were added to a suspension of 7-aza-5,6-dihydro-9-methoxy-3-nitro-5,11-dioxo-11H-indeno[1,2-c]-isoquinoline (6, 1.5 g, 4.64 mmol) in dry DMF (230 mL) at 0° C. After the reaction mixture had been warmed to room temperature and stirred for 3 h, a dark solution formed. The solution was cooled to −10° C.-0° C. in an ice-salt-water bath, and 1,3-dibromopropane (4.686 g, 23.2 mmol) was added. The solution was stirred for 30 h and the reaction quenched with water (200 mL). The product was extracted with ethyl acetate (5×200 mL). The combined extracts were washed with water (6×150 mL) and brine (3×100 mL), dried with sodium sulfate, and evaporated to dryness under reduced pressure. The residue was triturated with ether, filtered and washed with ether to provide compound 7 as a red solid (1.47 g, 72%): mp 170-172° C. $^1$H NMR (300 MHz, CDCl$_3$) δ 9.19 (d, J=2.4 Hz, 1H), 8.74 (d, J=8.9 Hz, 1H), 8.48 (dd, J=9.0, 2.3 Hz, 1H), 8.23 (d, J=2.6 Hz, 1H), 7.44 (d, J=2.7 Hz, 1H), 5.16-5.05 (m, 2H), 3.98 (s, 3H), 3.55 (t, J=6.8 Hz, 2H), 2.52-2.37 (m, 2H); ESIMS m/z (rel intensity) 444.0 (MH$^+$, 100).

Mitsunobu Approach.

7-Aza-5,6-dihydro-9-methoxy-3-nitro-5,11-dioxo-11H-indeno[1,2-c]-isoquinoline (6, 97 mg, 0.3 mmol) and triphenylphosphine (236 mg, 0.9 mmol) were diluted in THF (30 mL). 3-Bromopropanol (129 mg, 0.9 mmol) was added, followed by DIAD (182 mg, 0.9 mmol). The solution was stirred at room temperature for 60 h and the reaction mixture was concentrated to dryness. The solid was purified by flash column chromatography, eluting with hexane-ethyl acetate (2:1) to provide the product 7 a red solid (50 mg, 39%).

7-Aza-5,6-dihydro-6-[3-(4-pyrrolidine-1-yl)propyl]-9-methoxy-3-nitro-5,11-dioxo-11H-indeno[1,2-c]isoquinoline (8)

7-Aza-6-(3-bromopropyl)-5,6-dihydro-9-methoxy-3-nitro-5,11-dioxo-11H-indeno[1,2-c]isoquinoline (7, 133 mg, 0.3 mmol), pyrrolidine (214 mg, 3 mmol), NaI (10 mg, 0.03 mmol), and potassium carbonate (208 mg, 1.5 mmol) were diluted with 1,4-dioxane (20 mL). The resulting mixture was heated at reflux for 6 h. The solvent was evaporated under reduced pressure, and the residue was re-dissolved in chloroform (100 mL). The chloroform solution was washed with water (3×10 mL) and brine (20 mL), dried with sodium sulfate, and evaporated to dryness. The solid residue was subjected to column chromatography (silica gel), eluting with 5-20% methanol in dichloromethane to yield the red solid product 8 (88 mg, 68%): mp 248-250° C. IR (film) 3412, 1613, 1483, 1335, 1300 cm$^{-1}$; $^1$H NMR (300 MHz, CDCl$_3$) δ 9.17 (d, J=2.1 Hz, 1H), 8.78 (d, J=8.7 Hz, 1H), 8.52 (dd, J=9.0, 2.7 Hz, 1H), 8.27 (d, J=2.6 Hz, 1H), 7.45 (d, J=2.7 Hz, 1H), 5.07 (t, J=6.9 Hz, 2H), 3.99 (s, 3H), 3.87-3.83 (m, 2H), 3.28-3.23 (m, 2H), 2.85-2.80 (m, 2H), 2.55-2.49 (m, 2H), 2.28-2.23 (m, 2H), 2.10-2.07 (m, 2H); ESIMS m/z (rel intensity) 435.1 (MH$^+$, 100). HPLC purity: 99.42% (C$_{18}$ reverse phase, MeOH—H$_2$O, 85:15); HRMS-ESI m/z: MH$^+$ calcd for C$_{23}$H$_{23}$N$_4$O$_5$, 435.1669; found, 435.1656. HPLC purity: 99.42% (C$_{18}$ reverse phase, MeOH—H$_2$O, 85:15).

Mitsunobu Approach.

7-Aza-5,6-dihydro-9-methoxy-3-nitro-5,11-dioxo-11H-indeno[1,2-c]-isoquinoline (6, 97 mg, 0.3 mmol) and triphenylphosphine (236 mg, 0.9 mmol) were diluted in THF (30 mL). 3-(1-Pyrrolidinyl)-1-propanol (117 mg, 0.9 mmol) was added, followed by DIAD (182 mg, 0.9 mmol). The solution was stirred at room temperature for 72 h. The reaction mixture was concentrated to dryness. The solid was purified by flash column chromatography, eluting with 5-20% methanol in dichloromethane to yield the red solid product 8 (52 mg, 40%).

3-(1-Pyrrolidinyl)-1-propanol

Potassium carbonate (1.4 g, 0.94 mol) and pyrrolidine (0.87 mL, 1.8 mol) were added to a stirred solution of 3-bromopropanol (1 g, 0.635 mol) in 30 mL of THF at 0° C., and the resulting mixture was stirred at room temperature for 15 h. The resulting mixture was diluted with ethyl acetate (200 mL) and filtered through celite. The filtrate was concentrated, and the residue was subjected to column chromatography (silica gel), eluting with 50% methanol in dichloromethane, to yield a yellow oil (0.57 g, 70%). $^1$H NMR (300 MHz, CDCl$_3$) δ 3.79 (t, J=5.1 Hz, 2H), 2.71 (t, J=5.6 Hz, 2H), 2.57-2.51 (m, 4H), 1.75-1.66 (m, 6H); $^{13}$C NMR (125 MHz, CDCl$_3$) δ 64.18, 56.02, 54.09, 29.24, 23.27.

7-Aza-5,6-dihydro-6-[3-(3H-methylpiperazine-1-yl) propyl]-9-methoxy-3-nitro-5,11-dioxo-11H-indeno [1,2-c]isoquinoline (9)

Compound 7 (133 mg, 0.3 mmol), 1-methylpiperazine (300 mg, 3 mmol), NaI (10 mg, 0.03 mmol), and potassium carbonate (208 mg, 1.5 mmol) were diluted with 1,4-dioxane (20 mL). The resulting mixture was heated at reflux for 6 h. The solvent was evaporated under reduced pressure, and the residue was re-dissolved in chloroform (100 mL). The chloroform solution was washed with water (3×10 mL) and brine (20 mL), dried with sodium sulfate, and evaporated to dryness. The solid residue was subjected to column chromatography (silica gel), eluting with 5-20% methanol in dichloromethane, to yield the orange solid product (107 mg, 77%): mp 211-213° C. IR (film) 3429, 1666, 1500, 1334, 1286 cm$^{-1}$; $^1$H NMR (300 MHz, CDCl$_3$) δ 9.20 (d, J=2.3 Hz, 1H), 8.77 (d, J=8.9 Hz, 1H), 8.49 (dd, J=8.7, 2.6 Hz, 1H), 8.22 (d, J=2.6 Hz, 1H), 7.46 (d, J=2.7 Hz, 1H), 5.07 (t, J=6.9 Hz, 2H), 3.98 (s, 3H), 2.60-2.55 (m, 2H), 2.46-2.28 (m, 8H), 2.26 (s, 3H), 2.06-2.01 (m, 2H); ESIMS m/z (rel intensity) 464.1 (MH$^+$, 100); HRMS-ESI m/z: MH$^+$ calcd for C$_{24}$H$_{26}$N$_5$O$_5$, 464.1934; found, 464.1928. HPLC purity: 98.34% (C$_{18}$ reverse phase, MeOH—H$_2$O, 90:10).

7-Aza-5,6-dihydro-9-methoxy-3-nitro-5,11-dioxo-6-[3-(piperazine-1-yl)propyl]-11H-indeno[1,2-c]iso-quinoline (10)

Compound 7 (133 mg, 0.3 mmol), piperazine (258 mg, 3 mmol), NaI (10 mg, 0.03 mmol) and potassium carbonate (208 mg, 1.5 mmol) were diluted with 1,4-dioxane (20 mL). The resulting mixture was heated at reflux for 6 h. The solvent was evaporated under reduced pressure, and the residue was re-dissolved in chloroform (100 mL). The chloroform solution was washed with water (3×10 mL) and brine (20 mL), dried with sodium sulfate, and evaporated to dryness. The solid residue was subjected to column chromatography (silica gel), eluting with 5-20% methanol in dichloromethane, to yield the red solid product (88 mg, 66%): mp 134-135° C. IR (film) 3418, 2925, 1671, 1613, 1484, 1336 cm$^{-1}$; $^1$H NMR (300 MHz, CDCl$_3$) δ 9.18 (d, J=2.4 Hz, 1H), 8.78 (d, J=8.8 Hz, 1H), 8.46 (dd, J=8.9, 2.6 Hz, 1H), 8.20 (d, J=2.5 Hz, 1H), 7.44 (d, J=2.8 Hz, 1H), 5.06 (t, J=6.8 Hz, 2H), 3.95 (s, 3H), 2.58-2.54 (m, 2H), 2.43-2.25 (m, 8H), 2.04-1.98 (m, 2H); 1.91 (brs, 1H); ESIMS m/z (rel intensity) 450.1 (MH$^+$, 100); HRMS-ESI m/z: MH$^+$ calcd for C$_{23}$H$_{23}$N$_5$O$_5$, 450.1778; found, 450.1779. HPLC purity: 100% (C$_{18}$ reverse phase, MeOH—H$_2$O, 80:20).

7-Aza-5,6-dihydro-9-methoxy-6-[3-(methylamino-propyl]-3-nitro-5,11-dioxo-11H-indeno[1,2-c]isoqui-noline (11)

Compound 7 (133 mg, 0.3 mmol), NaI (10 mg, 0.03 mmol), methylamine (2M in THF) (3 mL, 6 mmol), and triethylamine (0.125 mL, 0.9 mmol) were diluted with anhydrous DMF (40 mL). The resulting mixture was stirred for 12 h at room temperature and the reaction quenched with water (5 mL). The products were extracted with chloroform (5×40 mL). The combined extracts were washed with water (6×20 mL) and brine (3×20 mL), dried with sodium sulfate, and evaporated to dryness under reduced pressure. The solid residue was subjected to column chromatography (silica gel), eluting with 5-20% methanol in dichloromethane containing 1% trimethylamine, to yield a red solid product (80 mg, 68%): mp 259-262° C. IR (film) 3435, 2964, 2782, 1682, 1555, 1481, 1336, 1302 cm$^1$; $^1$H NMR (300 MHz, CDCl$_3$) δ 9.18 (d, J=2.4 Hz, 1H), 8.75 (d, J=8.9 Hz, 1H), 8.48 (dd, J=8.70, 2.7 Hz, 1H), 8.23 (d, J=2.7 Hz, 1H), 7.43 (d, J=2.4 Hz, 1H), 5.03 (t, J=7.5 Hz, 2H), 3.97 (s, 3H), 2.77-2.72 (m, 2H), 2.45 (s, 3H), 2.09-1.96 (m, 3H); ESIMS m/z (rel intensity) 395.1 (MH$^+$, 100); HRMS-ESI m/z: MH$^+$ calcd for C$_{20}$H$_{18}$N$_4$O$_5$, 395.1356; found, 395.1357. HPLC purity: 96.98% (C$_{18}$ reverse phase, MeOH—H$_2$O, 85:15).

7-Aza-5,6-dihydro-6-[3-((4,5-dihydrothiazol-2-yl) amino)propyl]-9-methoxy-3-nitro-5,11-dioxo-11H-indeno[1,2-c]isoquinoline (12)

Compound 7 (106 mg, 0.24 mmol), 2-amino-2-thiazoline (333 mg, 2.4 mmol), NaI (9 mg, 0.024 mmol), and potassium carbonate (165 mg, 1.2 mmol) were diluted with 1,4-dioxane (30 mL). The resulting mixture was heated at reflux for 6 h. The solvent was evaporated under reduced pressure, and the residue was re-dissolved in chloroform (100 mL). The chloroform solution was washed with water (3×10 mL) and brine (20 mL), dried with sodium sulfate, and evaporated to dryness. The solid residue was subjected to column chromatography (silica gel), eluting with 5-20% methanol in dichloromethane, to yield the red solid product (63 mg, 57%): mp 175-177° C. IR (film) 3430, 1641, 1613, 1504, 1482, 1335 cm$^1$; $^1$H NMR (300 MHz, CDCl$_3$) δ 9.19 (d, J=2.2 Hz, 1H), 8.75 (d, J=8.9 Hz, 1H), 8.49 (dd, J=8.9, 2.1 Hz, 1H), 8.28 (d, J=2.7 Hz, 1H), 7.43 (d, J=2.8 Hz, 1H), 5.05 (t, J=5.2 Hz, 2H), 3.97 (s, 3H), 3.76 (t, J=6.7 Hz, 2H), 3.64 (t, J=6.5 Hz, 2H), 3.42 (t, J=7.5 Hz, 1H), 3.24 (t, J=6.7 Hz, 2H), 2.20-2.15 (m, 2H); ESIMS m/z (rel intensity) 466.1 (MH$^+$, 100); HRMS-ESI m/z: MH$^+$ calcd for $C_{22}H_{19}N_5O_5S$, 466.1185; found, 466.1182. HPLC purity: 97.50% ($C_{18}$ reverse phase, MeOH—H$_2$O, 90:10).

7-Aza-5,6-dihydro-9-methoxy-6-[3-((2-morpholinoethyl)amino)propyl]-3-nitro-5,11-dioxo-11H-indeno[1,2-c]isoquinoline (13)

Compound 7 (106 mg, 0.24 mmol), 4-(2-aminoethyl)morpholine (314 mg, 2.4 mmol), NaI (9 mg, 0.024 mmol), and potassium carbonate (165 mg, 1.2 mmol) were diluted with 1,4-dioxane (30 mL). The resulting mixture was heated at reflux for 6 h. The solvent was evaporated under reduced pressure, and the residue was re-dissolved in chloroform (100 mL). The chloroform solution was washed with water (3×10 mL) and brine (20 mL), dried with sodium sulfate, and evaporated to dryness. The solid residue was subjected to column chromatography (silica gel), eluting with 5-20% methanol in dichloromethane, to yield the red solid product (58 mg, 50%): mp 214-216° C. IR (film) 2770, 1437, 1332, 1219 cm$^{-1}$; $^1$H NMR (300 MHz, CDCl$_3$) δ 9.04 (d, J=2.2 Hz, 1H), 8.80 (d, J=8.9 Hz, 1H), 8.51 (dd, J=8.9, 2.1 Hz, 1H), 8.26 (d, J=2.7 Hz, 1H), 7.47 (d, J=2.8 Hz, 1H), 4.97 (t, J=5.3 Hz, 2H), 3.99 (s, 3H), 3.94-3.89 (m, 4H), 3.78 (t, J=6.5 Hz, 2H), 3.20-3.15 (m, 2H), 3.08-3.02 (m, 2H), 2.80-2.75 (m, 3H), 2.65 (m, 2H), 2.22-2.18 (m, 2H); ESIMS m/z (rel intensity) 494.2 (MH$^+$, 100); HRMS-ESI m/z: MH$^+$ calcd for $C_{25}H_{27}N_5O_6$, 494.2040; found, 494.2038. HPLC purity: 98.44% ($C_{18}$ reverse phase, MeOH—H$_2$O, 90:10).

7-Aza-5,6-dihydro-6-[3-(isopropylamino)propyl]-9-methoxy-3-nitro-5,11-dioxo-11H-indeno[1,2-c]isoquinoline (14)

Compound 7 (133 mg, 0.3 mmol), NaI (10 mg, 0.03 mmol), isopropylamine (177 mg, 6 mmol), and triethylamine (0.125 mL, 0.9 mmol) were diluted with anhydrous DMF (40 mL). The resulting mixture was stirred for 12 h at room temperature and the reaction quenched with water (5 mL). The products were extracted with chloroform (5×40 mL). The combined extracts were washed with water (6×20 mL) and brine (3×20 mL), dried with sodium sulfate, and evaporated to dryness under reduced pressure. The solid residue was subjected to column chromatography (silica gel), eluting with 5-20% methanol in dichloromethane containing 1% trimethylamine, to yield the red solid product (100 mg, 80%): mp 278-280° C. IR (film) 2961, 2805, 1677, 1610, 1337, 1288, 854 cm$^1$; $^1$H NMR (300 MHz, DMSO) δ 8.90 (d, J=2.1 Hz, 1H), 8.67 (d, J=8.9 Hz, 1H), 8.61 (dd, J=8.8, 2.3 Hz, 1H), 8.37 (d, J=2.4 Hz, 1H), 7.70 (d, J=2.7 Hz, 1H), 4.89 (t, J=7.5 Hz, 2H), 3.98 (s, 3H), 3.28-3.21 (m, 1H), 3.09-3.01 (m, 2H), 2.16-2.10 (m, 2H), 1.20 (d, J=6.5 Hz, 6H); ESIMS m/z (rel intensity) 423.2 (MH$^+$, 100); HRMS-ESI m/z: MH$^+$ calcd for $C_{22}H_{22}N_4O_5$, 423.1669; found, 423.1668. HPLC purity: 98.73% ($C_{18}$ reverse phase, MeOH—H$_2$O, 80:20).

7-Aza-6-[3-(ethylamino)propyl]-5,6-dihydro-9-methoxy-3-nitro-5,11-dioxo-11H-indeno[1,2-c]isoquinoline (15)

A mixture of compound 7 (133 mg, 0.3 mmol), anhydrous DMF (35 mL), NaI (10 mg, 0.03 mmol), ethylamine (3 mL of a 2 M solution in THF, 6 mmol), and triethylamine (0.125 mL, 0.9 mmol) was stirred for 12 h at room temperature and the reaction was then quenched with water (5 mL). The product was extracted with chloroform (6×40 mL). The combined extracts were washed with water (5×30 mL) and brine (3×20 mL), dried with sodium sulfate, and evaporated to dryness under reduced pressure. The solid residue was subjected to column chromatography (silica gel), eluting with 5-20% methanol in dichloromethane containing 1% trimethylamine, to yield the red solid product (89 mg, 73%): mp 266-268° C. IR (film) 3583, 2946, 1682, 1571, 1482, 1336, 1300 cm$^{-1}$; $^1$H NMR (300 MHz, DMSO) δ 8.89 (d, J=2.1 Hz, 1H), 8.65-8.59 (m, 2H), 8.36 (d, J=2.6 Hz, 1H), 7.69 (d, J=2.7 Hz, 1H), 4.89 (t, J=7.5 Hz, 2H), 3.98 (s, 3H), 3.08-3.01 (m, 2H), 2.97-2.89 (m, 2H), 2.15-2.09 (m, 2H), 1.17 (t, J=6.5 Hz, 3H); MALDI: m/z 409 (MH$^{+}$); HRMS-ESI m/z: MH$^+$ calcd for $C_{21}H_{20}N_4O_5$, 409.1512; found, 409.1516. HPLC purity: 98.32% ($C_{18}$ reverse phase, MeOH—H$_2$O, 90:10).

7-Aza-5,6-dihydro-6-[3-(4-(2-hydroxyethyl)piperazin-1-yl)propyl]-9-methoxy-3-nitro-5,11-dioxo-11H-indeno[1,2-c]isoquinoline (16)

Compound 7 (133 mg, 0.3 mmol), 1-(2-hydroxyethyl)piperazine (270 mg, 6 mmol), NaI (9 mg, 0.024 mmol), and potassium carbonate (165 mg, 1.2 mmol) were diluted with 1,4-dioxane (30 mL). The resulting mixture was heated at reflux for 6 h. The solvent was evaporated under reduced pressure, and the residue was re-dissolved in chloroform (120 mL). The chloroform solution was washed with water (3×10 mL) and brine (20 mL), dried with sodium sulfate, and evaporated to dryness. The solid residue was subjected to column chromatography (silica gel), eluting with 5-20% methanol in dichloromethane to yield the red solid product (78 mg, 53%): mp 214-216° C. IR (film) 3439, 1636, 1507, 1483, 1256 cm$^{-1}$; $^1$H NMR (300 MHz, CDCl$_3$) δ 9.20 (d, J=2.3 Hz, 1H), 8.76 (d, J=8.9 Hz, 1H), 8.50 (dd, J=8.7, 2.7 Hz, 1H), 8.21 (d, J=2.8 Hz, 1H), 7.44 (d, J=2.7 Hz, 1H), 4.90 (t, J=7.5 Hz, 2H), 3.98 (s, 3H), 3.59-3.55 (m, 2H), 2.97 (t, J=2.5 Hz, 1H), 2.59-2.44 (m, 12H), 2.08-2.03 (m, 2H); ESIMS m/z (rel intensity) 494.2 (MH$^+$, 100); HRMS-ESI m/z: MH$^+$ calcd for $C_{25}H_{27}N_5O_6$, 494.2040; found, 494.2041. HPLC purity: 96.97% ($C_{18}$ reverse phase, MeOH—H$_2$O, 90:10).

6-[3-(4-Aminopiperidin-1-yl)propyl]-7-aza-5,6-dihydro-9-methoxy-3-nitro-5,11-dioxo-11H-indeno[1,2-c]isoquinoline (17)

Compound 7 (133 mg, 0.3 mmol), 4-aminopiperidine (600 mg, 6 mmol), NaI (9 mg, 0.024 mmol), and potassium carbonate (165 mg, 1.2 mmol) were diluted with 1,4-dioxane (30 mL). The resulting mixture was heated at reflux for 6 h. The solvent was evaporated under reduced pressure, and the residue was re-dissolved in chloroform (140 mL). The chloroform solution was washed with water (3×10 mL) and brine (20 mL), dried with sodium sulfate, and evaporated to dryness. The solid residue was subjected to column chromatography (silica gel), eluting with 5-15% methanol in dichloromethane containing 1% trimethylamine to yield the red solid product (87 mg, 63%): mp 258-260° C. IR (film) 3440, 1641, 1436, 1335, 1301, 1084 cm$^{-1}$; $^1$H NMR (300 MHz, DMSO) δ 8.87 (d, J=2.2 Hz, 1H), 8.65-8.57 (m, 3H), 8.36 (d, J=2.6 Hz, 1H), 8.24 (d, J=2.3 Hz, 1H), 7.67 (d, J=2.6 Hz, 1H), 4.87 (t, J=7.4 Hz, 2H), 3.98 (s, 3H), 2.50-2.39 (m, 7H), 2.04-1.90 (m, 6H); ESIMS m/z (rel intensity) 464.1; HRMS-ESI m/z: MH$^+$ calcd for $C_{24}H_{26}N_5O_5$, 464.1934; found, 464.1919. HPLC purity: 95.10% ($C_{18}$ reverse phase, MeOH—$H_2O$, 80:20).

7-Aza-3-chloro-5,6-dihydro-9-methoxy-5-oxo-1H-indeno-[1,2-c]isoquinoline (13a)

5-Methoxy-3-methylpicolinonitrile (1.06 g, 7.2 mmol), NBS (1.41 g, 7.92 mmol), and AIBN (118 mg, 0.72 mmol) were diluted with 1,2-dichloroethane (40 mL) and the mixture was heated at reflux for 24 h. The reaction mixture was filtered and the filtrate was evaporated to dryness under reduced pressure to give crude 12a. The residue was re-dissolved in acetonitrile (70 mL). 7-Chloroisochroman-1,3-dione (11a, 2.12 g, 10.8 mmol) was added, followed by triethylamine (1.2 mL, 9.36 mmol), and the solution was heated at reflux for 24 h. The hot solution was filtered and the precipitate was washed with boiling acetonitrile (3×40 mL) to provide a gray solid 13a (698 mg, 32%): mp 258-262° C. The product was introduced into the next step without additional purification. APCIMS m/z (rel intensity): 299 (MH$^+$, 100).

7-Aza-3-fluoro-5,6-dihydro-9-methoxy-5-oxo 11H-indeno-[1,2-c]isoquinoline (13b). 5-Methoxy-3-methylpicolinonitrile (2.09 g, 14.12 mmol), NBS (2.6 g, 14.60 mmol), and AIBN (214 mg, 1.31 mmol) were diluted with $CCl_4$ (100 mL) and the mixture was heated at reflux for 24 h. The reaction mixture was filtered and the filtrate was evaporated to dryness under reduced pressure to give crude 12a. The residue was re-dissolved in acetonitrile (140 mL). 7-Fluoroisochroman-1,3-dione (11b, 2.8 g, 14.26 mmol) was added, followed by triethylamine (1.6 mL, 12.48 mL), and the solution was heated at reflux for 24 h. The hot solution was filtered and the precipitate was washed with boiling acetonitrile (3×60 mL) to provide a gray solid 13b (1.26 g, 31.6%): mp 304-310° C. The product was introduced into the next step without additional purification. $^1$H NMR (300 MHz, DMSO) δ 12.31 (s, 1H), 8.43-8.17 (m, 2H), 7.91 (ddd, J=14.1, 9.2, 4.0 Hz, 3H), 7.80-7.55 (m, 2H), 3.93 (s, 3H); APCIMS m/z (rel intensity) 283.0 (MH$^+$, 100).

7-Aza-3-chloro-5,6-dihydro-9-methoxy-5,11-dioxo-11H-indeno[1,2-c]isoquinoline (14a)

7-Aza-3-chloro-5,6-dihydro-9-methoxy-5-oxo-11H-indeno[1,2-c]isoquinoline (13a, 698 mg, 2.34 mmol) and $SeO_2$ (525 mg, 4.68 mmol) were diluted with 1,4-dioxane (40 mL) and the mixture was heated at reflux for 24 h. The reaction mixture was filtered while hot and the precipitate was washed with hot dioxane (4×30 mL). The combined filtrates were evaporated to dryness under reduced pressure to yield 14a (628 mg, 86%) as an orange solid: mp>300° C. IR (thin film) 3434, 1650, 1481, 1307, 1017 cm$^{-1}$; $^1$H NMR (300 MHz, DMSO) δ 8.38 (d, J=9.1 Hz, 1H), 8.25 (d, J=2.4 Hz, 1H), 8.10 (d, J=2.3 Hz, 1H), 7.87 (dd, J=9.3, 2.6 Hz, 1H), 7.54 (d, J=2.7 Hz, 1H), 3.92 (s, 3H); APCIMS m/z (rel intensity): 311.3 (MH$^+$, 100).

7-Aza-3-fluoro-5,6-dihydro-9-methoxy-5,11-dioxo-11H-indeno[1,2-c]isoquinoline (14b)

7-Aza-3-fluoro-5,6-dihydro-9-methoxy-5-oxo-11H-indeno-[1,2-c]isoquinoline (13b, 1.26 g, 4.47 mmol) and $SeO_2$ (0.94 g, 8.38 mmol) were diluted with 1,4-dioxane (170 mL) and the mixture was heated at reflux for 24 h. The reaction mixture was filtered while hot and the precipitate was washed with hot dioxane (3×50 mL). The combined filtrate was evaporated to dryness under reduced pressure to yield 14b as an orange solid (0.81 g, 40.5%): mp 331-334° C. $^1$H NMR (300 MHz, DMSO) δ 8.41 (dd, J=8.8, 5.4 Hz, 1H), 8.24 (d, J=2.6 Hz, 1H), 7.85 (dd, J=9.5, 2.8 Hz, 1H), 7.72 (dd, J=10.2, 7.4 Hz, 1H), 7.52 (d, J=2.7 Hz, 1H), 3.93 (s, 3H); IR (thin film) 2994, 1682, 1612, 1574, 1560, 1537 cm$^1$; ESIMS m/z (rel intensity) 295.0 (M-H, 100).

3-Chloro-6-(3-chloropropyl)-9-methoxy-5H-pyrido [3',2':4,5]cyclopenta[1,2-c]isoquinoline-5,11(6H)-dione (15a)

Sodium hydride (62 mg, 2.5 mmol) and sodium iodide (24 mg, 0.162 mmol) were added to a suspension of 7-aza-3-chloro-5,6-dihydro-9-methoxy-5,11-dioxo-11H-indeno[1,2-c]-isoquinoline (14a, 270 mg, 0.86 mmol) in dry DMF (30 mL) at 0° C. After the reaction mixture had been warmed to room temperature and stirred for 1.5 h, a dark-red solution formed. The solution was cooled to 0° C. again, and 1-bromo-3-chloropropane (0.4 g, 2.9 mmol) was added. The solution was stirred for 24 h and the reaction was quenched with water (100 mL), followed by extraction with chloroform (3×50 mL). The combined extracts were washed with water (3×50 mL) and brine (50 mL), dried with sodium sulfate, and evaporated to dryness under reduced pressure. The residue was triturated with diethyl ether to yield a red solid product (0.09 g, 26%): mp 195-197° C. IR (thin film) 3062, 1659, 1607, 1483 cm$^{-1}$; $^1$H NMR (300 MHz, CDCl$_3$) δ 8.25 (d, J=8.6 Hz, 1H), 8.01 (d, J=2.1 Hz, 1H), 7.84 (d, J=2.7 Hz, 1H), 7.36 (dd, J=8.7, 2.2 Hz, 1H), 7.09 (d, J=2.8 Hz, 1H), 4.82-4.67 (m, 2H), 3.65 (s, 3H), 3.24 (t, J=7.0 Hz, 2H), 2.18-2.03 (m, 2H); MALDIMS m/z (rel intensity) 389/391 (MH$^+$, 100); HRESIMS calcd for $C_{19}H_{15}Cl_2N_2O_3$ (MH$^+$) 389.0460, found 389.0452.

6-(3-Chloropropyl)-3-fluoro-9-methoxy-5H-pyrido [3',2':4,5]cyclopenta[1,2-c]isoquino-line-5,11(6H)-dione (15b)

Sodium hydride (90 mg, 3.56 mmol) and sodium iodide (26 mg, 0.18 mmol) were added to a suspension of 7-aza-3-fluoro-5,6-dihydro-9-methoxy-5,11-dioxo-11H-indeno[1,2-c] isoquinoline (14b, 0.536 g, 1.81 mmol) in dry DMF (45 mL) at 0° C. After the reaction mixture had been warmed to room temperature and stirred for 2 h, a dark-red solution was formed. The solution was cooled to 0° C. again, and 1-bromo-3-chloropropane (726 mg, 2.32 mmol) was added. The solution was stirred for 24 h and quenched with water (150 mL), followed by extraction with ethyl acetate (3×70 mL) and brine (1×70 mL), dried with sodium sulfate, and evaporated to dryness under reduced pressure. The residue was subjected to column chromatography (silica gel), eluting with hexane-ethyl acetate (2:1), to yield the red solid product (0.31 g, 46%): mp 244-248° C. IR (thin film) 3053, 1701, 1653, 1589, 1549, 1507, 1482, 1435, 1285 cm$^{-1}$; $^1$H NMR (300 MHz, DMSO) δ 8.50 (dd, J=8.9, 5.4 Hz, 1H), 8.26 (d, J=2.7 Hz, 1H), 7.87 (dd, J=9.5, 2.7 Hz, 1H), 7.73 (td, J=8.8, 2.9 Hz, 1H), 7.52 (d, J=2.8 Hz, 1H), 4.91 (t, J=7.1

Hz, 2H), 3.94 (s, 3H), 3.76 (t, J=6.7 Hz, 2H), 2.28-2.15 (m, 2H); MALDIMS m/z (rel intensity) 373.0 (MH+, 100); HRESIMS calcd for $C_{19}H_{15}ClFN_2O_3(MH^+)$ 373.0755, found 373.0748.

General Procedures for the Preparation of Compounds 16a-j.

Compound 15a (0.1 mmol), $K_2CO_3$ (0.05 g, 1 mmol), NaI (40 mg) and the appropriate amine (10 eq) were dissolved in DMF (5 mL). The mixture was stirred overnight at 90° C. and then cooled to room temperature. Water (10 mL) was added to the reaction mixture and then the mixture was extracted with EtOAc (3×10 mL). The combined organic layers were washed with water (3×15 mL) and brine (15 mL), dried over $Na_2SO_4$, and evaporated under vacuum. The residue was purified using silica gel column chromatography (MeOH—$CHCl_3$, 5:95).

3-Chloro-9-methoxy-6-(3-morpholinopropyl)-5H-pyrido[3',2':4,5]cyclopenta[1,2-c]isoquinoline-5,11(6H)-dione (16a)

This compound was isolated as a red powder (0.03 g, 66%): mp 253-256° C. IR (thin film) 3065, 2941, 2808, 1698, 1661, 1608, 1590, 1562, 1537, 1500 cm$^{-1}$; $^1$H NMR (300 MHz, DMSO-$d_6$) δ 8.47 (d, J=8.7 Hz, 1H), 8.26 (d, J=2.8 Hz, 1H), 8.13 (d, J=2.3 Hz, 1H), 7.88 (dd, J=8.7, 2.3 Hz, 1H), 7.59 (d, J=2.8 Hz, 1H), 4.83 (m, 2H), 3.94 (s, 3H), 3.89 (d, J=6.2 Hz, 2H), 3.73-3.56 (m, 3H), 3.20 (m, 2H), 3.03 (m, 3H), 2.20 (m, 2H); MALDIMS m/z (rel intensity) 440 (MH+, 100); HRESIMS calcd for $C_{23}H_{22}ClN_3O_4(MH^+)$ 440.1322, found 440.1372; HPLC purity, 96.2% (MeOH—$H_2O$, 85:15).

6-(3-(1H-Imidazol-1-yl)propyl)-3-chloro-9-methoxy-5H-pyrido[3',2':4,5]cyclopenta[1,2-c]isoquinoline-5,11(6H)-dione (16b)

This compound was isolated as an orange-red solid (0.018 g, 41%): mp 284-286° C. IR (thin film) 2918, 1696, 1673, 1607, 1566, 1535, 1501 cm$^{-1}$; $^1$H NMR (300 MHz, DMSO-$d_6$) δ 8.37 (d, J=8.7 Hz, 1H), 8.08 (s, 1H), 8.04 (d, J=2.2 Hz, 1H), 7.78 (d, J=6.3 Hz, 1H), 7.62-7.48 (m, 1H), 7.46 (d, J=2.7 Hz, 1H), 7.17-7.01 (m, 1H), 6.85-6.70 (m, 1H), 4.71 (m, 2H), 4.02 (m, 2H), 2.10 (m, 2H); MALDIMS m/z (rel intensity) 421 (MH+, 100); HRESIMS calcd for $C_{22}H_{17}ClN_4O_3(MH^+)$ 421.1068, found 421.1059; HPLC purity, 97.17% (MeOH—$H_2O$, 85:15).

3-Chloro-6-(3-((4,5-dihydrothiazol-2-yl)amino)propyl)-9-methoxy-5H-pyrido[3',2':4,5]cyclopenta[1,2-c]isoquinoline-5,11(6H)-dione (16c)

This compound was isolated as a red solid (0.012 g, 25%): mp 295-298° C. IR (thin film) 2924, 1666, 1605, 1536, 1501 cm$^{-1}$; $^1$H NMR (300 MHz, DMSO-$d_6$) δ 8.50 (d, J=8.5 Hz, 1H), 8.26 (d, J=2.8 Hz, 1H), 8.15 (d, J=2.0 Hz, 1H), 7.90 (d, J=8.7 Hz, 1H), 7.62 (d, J=2.8 Hz, 1H), 4.85 (m, 2H), 4.06 (m, 2H), 3.96 (s, 3H), 3.88-3.78 (m, 1H), 3.70-3.62 (m, 2H), 3.55-3.38 (m, 2H), 2.09 (m, 2H). MALDIMS m/z (rel intensity) 457 (MH+, 100), 455; HRESIMS calcd for $C_{22}H_{19}ClN_4O_3S$ (MH+) 455.0945, found 455.0928; HPLC purity, 100% (MeOH—$H_2O$, 85:15).

3-Chloro-6-(3-(4-hydroxypiperidin-1-yl)propyl)-9-methoxy-5H-pyrido[3',2':4,5]cyclopenta-[1,2-c]isoquinoline-5,11(6H)-dione (16d)

This compound was isolated as deep red solid (0.18 g, 38%): mp 279-281° C. IR (thin film) 3320, 2940, 1698, 1666, 1610, 1589, 1563, 1538, 1500 cm$^{-1}$; $^1$H NMR (300 MHz, DMSO-$d_6$) δ 8.44 (d, J=8.7 Hz, 1H), 8.24 (d, J=2.8 Hz, 1H), 8.11 (d, J=2.3 Hz, 1H), 7.84 (dd, J=8.7, 2.3 Hz, 1H), 7.53 (d, J=2.7 Hz, 1H), 4.87 (m, 2H), 4.58-4.49 (m, 1H), 3.92 (s, 3H), 2.60-2.58 (m, 2H), 1.90-1.85 (m, 2H), 1.49-1.42 (m, 2H), 1.16-1.00 (m, 2H); MALDIMS m/z (rel intensity) 454 (MH+, 100); HRESIMS calcd for $C_{24}H_{24}ClN_3O_4(MH^+)$ 454.1534, found 454.1524; HPLC purity, 96.77% (MeOH—$H_2O$, 85:15).

3-Chloro-9-methoxy-6-(3-(piperazin-1-yl)propyl)-5H-pyrido[3',2':4,5]cyclopenta[1,2-c]isoquinoline-5,11(6H)-dione (16e)

This compound was isolated as a red powder (0.044 g, 78%): mp 264-268° C. IR (thin film) 2937, 2808, 2469, 1697, 1669, 1606, 1565, 1536, 1502 cm$^{-1}$; $^1$H NMR (300 MHz, DMSO-$d_6$) δ 8.46 (d, J=8.7 Hz, 1H), 8.25 (d, J=2.7 Hz, 1H), 8.12 (d, J=2.3 Hz, 1H), 7.86 (dd, J=8.7, 2.3 Hz, 1H), 7.56 (d, J=2.8 Hz, 1H), 4.87 (m, 2H), 4.10 (m, 2H), 3.94 (s, 3H), 2.76 (m, 4H), 2.35 (m, 4H), 1.89 (m, 2H); MALDIMS m/z (rel intensity) 439 (MH+, 100); HRESIMS calcd for $C_{23}H_{23}ClN_4O_3(MH^+)$ 439.1537, found 439.1525; HPLC purity, 98.56% (MeOH—$H_2O$, 85:15).

3-Chloro-9-methoxy-6-(3-(isopropylamino)propyl)-5H-pyrido[3',2':4,5]cyclopenta[1,2-c]isoquinoline-5,11(6H)-dione (16f)

The reaction to prepare this compound was performed in a 45 mL pressure vessel and the product was isolated as red powder (0.032 g, 60%): mp 250-251° C. IR (thin film) 3065, 2942, 2782, 1700, 1664, 1609, 1590, 1563, 1539, 1499 cm$^{-1}$; $^1$H NMR (300 MHz, DMSO-$d_6$) δ 8.46 (d, J=8.6 Hz, 1H), 8.28 (s, 1H), 8.13 (s, 1H), 7.89 (d, J=8.5 Hz, 1H), 7.58 (s, 1H), 4.85 (m, 2H), 3.95 (s, 3H), 3.06 (s, 1H), 2.88 (m, 2H), 2.03 (m, 2H), 1.10 (d, J=5.6 Hz, 6H); MALDIMS m/z (rel intensity) 412 (MH+, 100); HRESIMS calcd for $C_{22}H_{22}ClN_3O_3(MH^{+})$ 412.1428, found 412.1420; HPLC purity, 100.00% (MeOH—$H_2O$, 85:15).

3-Chloro-9-methoxy-6-(3-(methylamino)propyl)-5H-pyrido[3',2':4,5]cyclopenta[1,2-c]isoquinoline-5,11(6H)-dione (16g)

The reaction to prepare this compound was performed in a 45 mL pressure vessel and the product was isolated as red powder (0.038 g, 77%): mp 274-275° C. IR (thin film) 2941, 2777, 1699, 1669, 1608, 1565, 1535, 1500 cm$^{-1}$; $^1$H NMR (300 MHz, DMSO-$d_6$) δ 8.48 (d, J=8.7 Hz, 1H), 8.29 (d, J=2.7 Hz, 1H), 8.15 (d, J=2.4 Hz, 1H), 7.90 (d, J=8.6 Hz, 1H), 7.60 (d, J=2.7 Hz, 1H), 4.85 (m, 2H), 3.95 (s, 3H), 3.33 (s, 3H), 2.91 (m, 2H), 2.05 (m, 2H); MALDIMS m/z (rel intensity) 384 (MH+, 100); HRESIMS calcd for $C_{20}H_{18}ClN_3O_3(MH^+)$ 384.1115, found 384.1108; HPLC purity, 95.81% (MeOH—$H_2O$, 85:15).

3-Chloro-9-methoxy-6-(3-(ethylamino)propyl)-5H-pyrido[3',2':4,5]cyclopenta[1,2-c]isoquinoline-5,11(6H)-dione (16h)

The reaction to prepare this compound was performed in a 45 mL pressure vessel and the product was isolated as red powder (0.04 g, 80%): mp 264-266° C. IR (thin film) 2945, 2756, 2497, 1710, 1661, 1608, 1566, 1537, 1499 cm$^{-1}$; $^1$H NMR (300 MHz, DMSO-$d_6$) δ 8.47 (d, J=8.7 Hz, 1H), 8.28 (d, J=2.7 Hz, 1H), 8.14 (d, J=2.3 Hz, 1H), 7.88 (dd, J=8.7, 2.3 Hz, 1H), 7.57 (d, J=2.7 Hz, 1H), 4.84 (d, J=7.0 Hz, 2H), 3.96 (s, 3H), 2.83 (t, J=7.4 Hz, 2H), 2.73 (q, J=7.3 Hz, 2H), 2.00 (m, 2H), 1.06 (t, J=7.2 Hz, 3H); MALDIMS m/z (rel intensity) 398 (MH$^+$, 100); HRESIMS calcd for $C_{21}H_{20}ClN_3O_3$(MH$^+$) 398.1272, found 398.1258; HPLC purity, 97.07% (MeOH—H$_2$O, 85:15).

3-Chloro-9-methoxy-6-(3-(pyrrolidin-1-yl)propyl)-5H-pyrido[3',2':4,5]cyclopenta[1,2-c]isoquinoline-5,11(6H)-dione (16i)

This compound was isolated as red powder (0.045 g, 83%): mp 242-244° C. IR (thin film) 3063, 2934, 2787, 1699, 1664, 1608, 1565, 1537, 1501 cm$^{-1}$; $^1$H NMR (300 MHz, DMSO-d$_6$) δ 8.45 (d, J=8.7 Hz, 1H), 8.27 (d, J=2.7 Hz, 1H), 8.12 (d, J=2.2 Hz, 1H), 7.86 (dd, J=8.7, 2.3 Hz, 1H), 7.55 (d, J=2.8 Hz, 1H), 4.90 (m, 2H), 4.11 (m, 2H), 3.95 (s, 3H), 3.16 (d, J=5.1 Hz, 4H), 1.96 (m, 2H), 1.57 (m, 4H); MALDIMS m/z (rel intensity) 424 (MH$^+$, 100); HRESIMS calcd for $C_{23}H_{22}ClN_3O_3$(MH$^+$) 424.1428, found 424.1419; HPLC purity, 96.93% (MeOH—H$_2$O, 85:15).

3-Chloro-9-methoxy-6-(3-(4-methylpiperazin-1-yl)propyl)-5H-pyrido[3',2':4,5]cyclopenta[1,2-c]isoquinoline-5,11(6H)-dione (16j)

This compound was isolated as red powder (0.042 g, 72%): mp 253-255° C. IR (thin film) 2931, 2789, 1699, 1666, 1607, 1565, 1537, 1501 cm$^1$; $^1$H NMR (300 MHz, DMSO-d$_6$) δ 8.42 (d, J=8.8 Hz, 1H), 8.23 (d, J=2.8 Hz, 1H), 8.08 (d, J=2.2 Hz, 1H), 7.83 (dd, J=8.7, 2.3 Hz, 1H), 7.51 (d, J=2.7 Hz, 1H), 4.89 (m, 2H), 3.93 (s, 3H), 2.37 (m, 2H), 2.12 (m, 8H), 1.96 (s, 3H), 1.87 (m, 2H); MALDIMS m/z (rel intensity) 453 (MH$^+$, 100); HRESIMS calcd for $C_{24}H_{25}ClN_4O_3$(MH$^+$) 453.1694, found 453.1686; HPLC purity, 95.88% (MeOH—H$_2$O, 85:15).

General Procedures for Preparation of Compounds 17a-i.

Compound 15b (50 mg, 0.134 mmol), K$_2$CO$_3$ (0.05 g, 1 mmol), NaI (40 mg) and the appropriate amine (10 eq) were mixed in DMF (5 mL). The mixture was stirred overnight at 90° C. and then cooled to room temperature. Water (30 mL) was added to the reaction flask and then the mixture was extracted with EtOAc (3×10 mL). The combined organic layers were washed with water (3×15 mL) and brine (15 mL), dried over Na$_2$SO$_4$, and evaporated to give a red residue. The residue was purified by silica gel column chromatography (MeOH—CHCl$_3$, 5:95) to yield compounds 17a-i. Compounds 17f-h were prepared using the same procedures but the reaction was performed in a 15 mL pressure vessel.

3-Fluoro-9-methoxy-6-(3-morpholinopropyl)-5H-pyrido[3',2':4,5]cyclopenta[1,2c]-isoquinoline-5,11(6H)-dione (17a)

This compound was isolated as a dark red solid (46 mg, 84%): mp 175-178° C. IR (thin film) 3070, 2856, 2806, 1698, 1658, 1593, 1548, 1511 cm$^1$; $^1$H NMR (300 MHz, DMSO-d$_6$) δ 8.50 (dd, J=9.0, 5.4 Hz, 1H), 8.22 (d, J=2.8 Hz, 1H), 7.86 (dd, J=9.5, 2.7 Hz, 1H), 7.72 (td, J=8.8, 2.8 Hz, 1H), 7.52 (d, J=2.7 Hz, 1H), 4.88 (t, J=7.4 Hz, 2H), 3.94 (s, 3H), 3.34 (m, 4H), 2.40 (t, J=6.4 Hz, 2H), 2.20 (m, 4H), 1.91 (d, J=6.7 Hz, 2H); MALDI m/z (rel intensity) 424 (MH$^+$, 100); HRMS-ESI m/z MH$^+$ calcd for $C_{23}H_{23}FN_3O_4$, 424.1673; found, 424.1665; HPLC purity: 96.06% (MeOH—H$_2$O, 85:15).

6-(3-(1H-Imidazol-1-yl)propyl)-3-fluoro-9-methoxy-5H-pyrido[3',2':4,5]-cyclo-penta[1,2-c]isoquinoline-5,11(6H)-dione (17b)

This compound was isolated as a dark red solid (37.5 mg, 69%): mp 176-180° C. IR (thin film) 3543, 2969, 1707, 1657, 1592, 1572, 1508 cm$^{-1}$; $^1$H NMR (300 MHz, DMSO-d$_6$) δ 8.53 (dd, J=9.0, 5.4 Hz, 1H), 8.15 (d, J=2.8 Hz, 1H), 7.95-7.69 (m, 2H), 7.55 (d, J=2.8 Hz, 1H), 7.28 (s, 1H), 6.98 (s, 1H), 4.81 (t, J=7.4 Hz, 2H), 4.14 (t, J=7.0 Hz, 2H), 3.95 (s, 3H), 2.27-2.16 (m, 2H); MALDI m/z (rel intensity) 405 (MH$^+$, 100); HRMS-ESI m/z MH$^+$ calcd for $C_{22}H_{18}FN_4O_3$, 405.1363; found, 405.1357; HPLC purity: 96.60% (MeOH—H$_2$O, 85:15).

6-(3-((4,5-Dihydrothiazol-2-yl)amino)propyl)-3-fluoro-9-methoxy-5H-pyrido[3',2':4,5]-cyclopenta-[1,2-c]isoquinoline-5,11(6H)-dione (17c)

This compound was isolated as a dark red solid (25 mg, 43%): mp 226-250° C. IR (thin film) 2937, 1699, 1657, 1593, 1549, 1510 cm$^{-1}$; $^1$H NMR (300 MHz, DMSO-d$_6$) δ 8.56 (d, J=5.5 Hz, 1H), 8.25 (d, J=2.7 Hz, 1H), 7.90 (d, J=9.5 Hz, 1H), 7.79 (d, J=8.8 Hz, 1H), 7.59 (d, J=2.7 Hz, 1H), 4.85 (m, 2H), 4.03 (d, J=7.3 Hz, 2H), 3.96 (s, 3H), 3.68 (m, 2H), 3.51 (d, J=7.4 Hz, 2H), 2.09 (m, 2H); ESIMS m/z (rel intensity) 439 (MH$^+$, 100); HRMS-ESI m/z MH$^+$ calcd for $C_{22}H_{20}FN_4O_3S$, 439.1240; found, 439.1233; HPLC purity: 95.01% (MeOH—H$_2$O, 85:15).

3-Fluoro-6-(3-(4-hydroxypiperidin-1-yl)propyl)-9-methoxy-5H-pyrido[3',2':4,5]-cyclopenta[1,2-c]-isoquinoline-5,11(6H)-dione (17d)

This compound was isolated as a dark red solid (30 mg, 50%): mp 205-209° C. IR (thin film) 3263, 2942, 1668, 1591, 1551, 1510 cm$^{-1}$; $^1$H NMR (300 MHz, DMSO-d$_6$) δ 8.54-8.44 (m, 1H), 8.24 (d, J=2.1 Hz, 1H), 7.87 (d, J=6.9 Hz, 1H), 7.73 (s, 1H), 7.53 (s, 1H), 4.88 (m, 2H), 4.47 (m, 1H), 3.94 (s, 3H), 2.57 (m, 1H), 2.40 (m, 2H), 1.89 (m, 4H), 1.50 (m, 2H), 1.07 (m, 2H); ESIMS m/z (rel intensity) 437 (MH$^+$, 100); HRMS-ESI m/z MH$^+$ calcd for $C_{24}H_{24}FN_3O_4$, 437.1989; found, 437.1981; HPLC purity: 95.24% (MeOH—H$_2$O, 85:15).

3-Fluoro-9-methoxy-6-(3-(piperazin-1-yl)propyl)-5H-pyrido[3',2':4,5]cyclopenta-[1,2-c]isoquinoline-5,11(6H)-dione (17e)

This compound was isolated as a dark red solid (44 mg, 78%): mp 237-239° C. IR (thin film) 2936, 2808, 1699, 1658, 1593, 1550, 1510 cm$^{-1}$; $^1$H NMR (300 MHz, DMSO-d$_6$) δ 8.51 (dd, J=9.0, 5.4 Hz, 1H), 8.23 (d, J=2.8 Hz, 1H), 7.86 (dd, J=9.5, 2.8 Hz, 1H), 7.73 (td, J=8.8, 2.8 Hz, 1H), 7.53 (d, J=2.8 Hz, 1H), 4.87 (t, J=7.3 Hz, 2H), 3.94 (s, 3H), 2.69 (m, 4H), 2.43 (t, J=6.5 Hz, 2H), 2.30 (m, 4H), 1.90 (t, J=6.9 Hz, 2H); MALDI m/z (rel intensity) 423 (MH$^+$, 100); HRMS-ESI m/z MH$^+$ calcd for $C_{23}H_{23}N_4O_3F$, 423.1833; found, 423.1824; HPLC purity: 95.28% (MeOH—H$_2$O, 85:15).

3-Fluoro-6-(3-(isopropylamino)propyl)-9-methoxy-5H-pyrido[3',2':4,5]cyclopenta[1,2-c]isoquinoline-5,11(6H)-dione (17f)

This compound was isolated as a dark red solid (41 mg, 75%): mp 285-292° C. IR (thin film) 2714, 1705, 1659, 1588, 1552, 1511 cm$^{-1}$; $^1$H NMR (300 MHz, DMSO-d$_6$) δ 8.52 (dd, J=8.9, 5.5 Hz, 1H), 8.36-8.22 (m, 2H), 7.89 (dd, J=9.4, 2.8 Hz, 1H), 7.75 (td, J=8.7, 2.7 Hz, 1H), 7.57 (t, J=2.5 Hz, 1H), 4.85 (t, J=7.1 Hz, 2H), 3.95 (s, 3H), 3.05 (m, 1H), 2.86 (d, J=7.8 Hz, 2H), 2.04 (m, 2H), 1.10 (d, J=6.5 Hz, 6H); MALDI m/z (rel intensity) 396 (MH$^+$, 100); HRMS-ESI m/z MH$^+$ calcd for C$_{22}$H$_{23}$FN$_3$O$_3$, 396.1724; found, 396.1719; HPLC purity: 96.70% (MeOH—H$_2$O, 85:15).

3-Fluoro-9-methoxy-6-(3-(methylamino)propyl)-5H-pyrido[3′,2′:4,5]cyclopenta[1,2-c]isoquinoline-5,11(6H)-dione (17g)

This compound was isolated as a dark red solid (31 mg, 63%): mp 259-265° C. IR (thin film) 1667, 1554, 1513, 1484, 1454 cm$^{-1}$; $^1$H NMR (300 MHz, DMSO-d$_6$) δ 8.56 (dd, J=8.9, 5.3 Hz, 1H), 8.29 (d, J=2.7 Hz, 1H), 7.92 (dd, J=9.4, 2.7 Hz, 1H), 7.86-7.75 (m, 1H), 7.61 (d, J=2.7 Hz, 1H), 4.87 (m, 2H), 3.96 (s, 3H), 3.00 (t, J=7.7 Hz, 2H), 2.54 (s, 3H), 2.11 (m, 2H); ESIMS m/z (rel intensity) 368 (MH$^+$, 100); HRMS-ESI m/z MH$^+$ calcd for C$_{20}$H$_{19}$FN$_3$O$_3$, 368.1411; found, 368.1402; HPLC purity: 95.05% (MeOH—H$_2$O, 85:15).

6-(3-(Ethylamino)propyl)-3-fluoro-9-methoxy-5H-pyrido[3′,2′:4,5]cyclopenta[1,2-c]isoquinoline-5,11(6H)-dione (17h)

This compound was isolated as a dark red solid (18.8 mg, 37.1%): mp 286-288° C. IR (thin film) 3451, 2924, 2851. 2783, 1700, 1671, 1616, 1592, 1573, 1552, 1511 cm$^{-1}$; $^1$H NMR (300 MHz, DMSO-d$_6$) δ 8.55 (dd, J=9.0, 5.5 Hz, 1H), 8.27 (d, J=2.8 Hz, 1H), 7.91 (dd, J=9.4, 2.8 Hz, 1H), 7.84-7.72 (m, 1H), 7.60 (d, J=2.8 Hz, 1H), 4.86 (t, J=6.9 Hz, 2H), 3.96 (s, 3H), 3.04-2.82 (m, 4H), 2.10 (d, J=8.2 Hz, 2H), 1.26-1.08 (m, 3H); MALDI m/z (rel intensity) 382 (MH$^+$, 100); HRMS-ESI m/z MH$^+$ calcd for C$_{21}$H$_{21}$FN$_3$O$_3$, 382.1567; found, 382.1558; HPLC purity: 95.58% (MeOH—H$_2$O, 85:15).

3-Fluoro-9-methoxy-6-(3-(pyrrolidin-1-yl)propyl)-5H-pyrido[3′,2′:4,5]cyclopenta[1,2-c]isoquinoline-5,11(6H)-dione (17i)

This compound was isolated as a dark red solid (20 mg, 37%): mp 157-162° C. IR (thin film) 1702, 1663, 1614, 1572, 1550, 1510, 1480, 1446, 1434 cm$^{-1}$; $^1$H NMR (300 MHz, DMSO-d$_6$) δ 8.51 (dd, J=8.9, 5.4 Hz, 1H), 8.26 (t, J=2.6 Hz, 1H), 7.88 (dd, J=9.5, 2.8 Hz, 1H), 7.74 (td, J=8.7, 2.8 Hz, 1H), 7.54 (t, J=2.5 Hz, 1H), 4.90 (t, J=6.9 Hz, 2H), 3.95 (s, 3H), 2.73 (m, 4H), 1.98 (m, 3H), 1.60 (m, 5H); ESIMS m/z (rel intensity) 408 (MH$^+$, 100); HRMS-ESI m/z MH$^+$ calcd for C$_{27}$H$_{23}$FN$_3$O$_3$, 408.1724; found, 408.1717; HPLC purity: 95.08%. (MeOH—H$_2$O, 85:15).

Topoisomerase I-Mediated DNA Cleavage Reactions (Dexheimer, et al., *Nat. Protoc.* 2008, 3, 1736-1750). A 3′-[$^{32}$P]-labeled 117-bp DNA oligonucleotide was prepared as previously described. The oligonucleotide contains previously identified Top1 cleavage sites in 161-bp pBluescript SK(−) phagemid DNA. Approximately 2 nM radiolabeled DNA substrate was incubated with recombinant Top1 in 20 μL of reaction buffer [10 mM Tris-HCl (pH 7.5), 50 mM KCl, 5 mM MgCl$_2$, 0.1 mM EDTA, and 15 μg/mL BSA] at 25° C. for 20 min in the presence of various concentrations of test compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromophenol blue). Aliquots of each reaction mixture were subjected to 20% denaturing PAGE. Gels were dried and visualized by using a phosphoimager and ImageQuant software (Molecular Dynamics). Cleavage sites are numbered to reflect actual sites on the 117 bp oligonucleotide (Antony, et al., *Nucleic Acids Res.* 2007, 35, 4474-4484).

Recombinant Tdp1 Assay (Nguyen, et al., *J. Med. Chem.* 2012, 55, 4457-4478). A 5′-[$^{32}$P]-labeled single-stranded DNA oligonucleotide containing a 3′-phosphotyrosine (N14Y) was incubated at 1 nM with 10 pM recombinant TDP1 in the absence or presence of inhibitor for 15 min at room temperature in the LMP1 assay buffer containing 50 mM Tris HCl, pH 7.5, 80 mM KCl, 2 mM EDTA, 1 mM DTT, 40 μg/mL BSA, and 0.01% Tween-20. Reactions were terminated by the addition of 1 volume of gel loading buffer [99.5% (v/v) formamide, 5 mM EDTA, 0.01% (w/v) xylene cyanol, and 0.01% (w/v) bromophenol blue]. Samples were subjected to a 16% denaturing PAGE with multiple loadings at 12-min intervals. Gels were dried and exposed to a PhosphorImager screen (GE Healthcare). Gel images were scanned using a Typhoon 8600 (GE Healthcare), and densitometry analyses were performed using the ImageQuant software (GE Healthcare).

Recombinant Tdp2 Assay (Gao, et al., *J. Biol. Chem.* 2012, 287, 30842-30852). TDP2 reactions were carried out as described previously with the following modifications. The 18-mer single-stranded oligonucleotide DNA substrate (TY18, α$^{32}$P-cordycepin-3′-labeled) was incubated at 1 nM with 25 pM recombinant human TDP2 in the absence or presence of inhibitor for 15 min at room temperature in the LMP2 assay buffer containing 50 mM Tris-HCl, pH 7.5, 80 mM KCl, 5 mM MgCl$_2$, 0.1 mM EDTA, 1 mM DTT, 40 μg/mL BSA, and 0.01% Tween 20. Reactions were terminated and treated similarly to whole-cell extract and recombinant Tdp1 reactions (see previous paragraph).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:
1. A compound of formula (II)

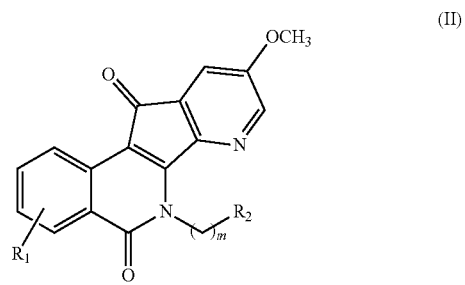

or a pharmaceutically acceptable salt thereof, wherein m is 3, $R^1$ is 3-Cl or 3-F, and $R^2$ is selected from the group consisting of

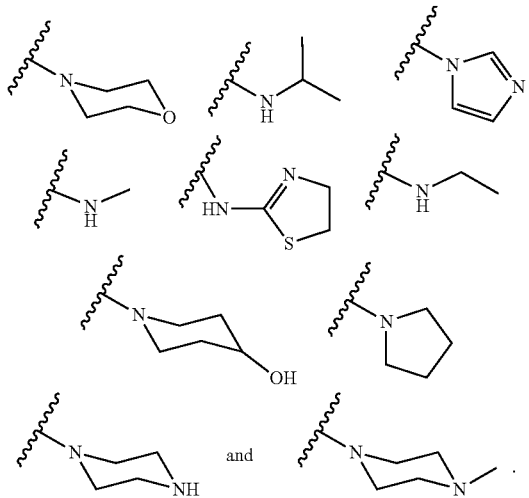

2. The compound or salt of claim 1 wherein $R^1$ is 3-F.
3. The compound or salt of claim 1 wherein $R^1$ is 3-Cl.
4. The compound or salt of claim 2 wherein $R^2$ is MeHN—, EtHN—, or i-PrHN—.
5. The compound or salt of claim 3 wherein $R^2$ is MeHN—, EtHN—, or i-PrHN—.

6. A pharmaceutical composition comprising the compound of claim 1, or a pharmaceutically acceptable salt thereof, and one or more pharmaceutically acceptable carriers, diluents, and excipients.

7. A method for treating a patient with a cancer selected from the group consisting of lung cancer, colon cancer, a CNS cancer, melanoma, ovarian cancer, renal cancer, prostate cancer, and breast cancer, the method comprising the step of administering a therapeutically effective amount of the pharmaceutical composition of claim 6 to the patient in need of relief from said cancer.

8. A method for treating a patient with a cancer selected from the group consisting of lung cancer, colon cancer, a CNS cancer, melanoma, ovarian cancer, renal cancer, prostate cancer, and breast cancer, the method comprising the step of administering a therapeutically effective amount of the compound or salt of claim 1, together with one or more pharmaceutically acceptable carriers, diluents, and excipients, to the patient in need of relief from said cancer.

9. A method for treating a patient with a cancer selected from the group consisting of lung cancer, colon cancer, a CNS cancer, melanoma, ovarian cancer, renal cancer, prostate cancer, and breast cancer, the method comprising the step of administering a therapeutically effective amount of the compound or salt of claim 1, and a therapeutically effective amount of one or more other compounds of the same or different mode of action, together with one or more pharmaceutically acceptable carriers, diluents, and excipients, to the patient in need of relief from said cancer.

* * * * *